(12) United States Patent
Martin et al.

(10) Patent No.: US 11,932,838 B2
(45) Date of Patent: Mar. 19, 2024

(54) CELL CULTURE MEDIA EXTENDING MATERIALS AND METHODS

(71) Applicant: CORNING INCORPORATED, Corning, NY (US)

(72) Inventors: Gregory Roger Martin, Acton, ME (US); Allison Jean Tanner, Portsmouth, NH (US); Alexander Meyer Wilks, Corrales, NM (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 17/746,473

(22) Filed: May 17, 2022

(65) Prior Publication Data
US 2022/0411735 A1 Dec. 29, 2022

Related U.S. Application Data

(63) Continuation of application No. 15/528,644, filed as application No. PCT/US2015/061740 on Nov. 20, 2015, now abandoned.

(60) Provisional application No. 62/084,356, filed on Nov. 25, 2014.

(51) Int. Cl.
*C12M 1/24* (2006.01)
*C12M 1/00* (2006.01)
*C12N 5/071* (2010.01)

(52) U.S. Cl.
CPC ............ *C12M 23/08* (2013.01); *C12M 23/20* (2013.01); *C12N 5/0682* (2013.01)

(58) Field of Classification Search
None
See application file for complete search history.

(56) References Cited

U.S. PATENT DOCUMENTS

| | | | |
|---|---|---|---|
| 3,926,723 A | 12/1975 | Green et al. | |
| 4,657,867 A * | 4/1987 | Guhl ...................... | C12M 23/38 435/305.3 |
| 4,793,474 A | 12/1988 | Drake | |
| 5,010,685 A | 4/1991 | Sakamoto et al. | |
| 5,153,131 A | 10/1992 | Wolf et al. | |
| 5,155,035 A | 10/1992 | Schwarz et al. | |
| 5,576,211 A | 11/1996 | Falkenberg et al. | |
| 6,080,581 A | 6/2000 | Anderson et al. | |
| 6,156,570 A | 12/2000 | Hu et al. | |
| 6,190,913 B1 | 2/2001 | Singh | |
| 6,372,494 B1 | 4/2002 | Naughton et al. | |
| 6,607,910 B1 | 8/2003 | Dimitrijevich et al. | |
| 7,927,869 B2 | 4/2011 | Rosero | |
| 7,942,867 B2 | 5/2011 | Hood et al. | |
| 8,398,980 B2 | 3/2013 | Kano et al. | |
| 8,481,308 B2 | 7/2013 | Stern et al. | |
| 8,563,066 B2 | 10/2013 | Sexton et al. | |
| 8,568,720 B2 | 10/2013 | Morichika et al. | |
| 8,580,264 B2 | 11/2013 | Zhang et al. | |
| 8,865,465 B2 | 10/2014 | Baker et al. | |
| 2001/0049141 A1 | 12/2001 | Fike et al. | |
| 2003/0087409 A1 | 5/2003 | Bandman et al. | |
| 2003/0153079 A1 | 8/2003 | Fike et al. | |
| 2004/0087022 A1 | 5/2004 | Fike et al. | |
| 2004/0161842 A1 | 8/2004 | Daugulis et al. | |
| 2004/0209360 A1 * | 10/2004 | Keith .................. | C12N 5/0068 427/2.11 |
| 2004/0209361 A1 | 10/2004 | Hemperly et al. | |
| 2006/0211101 A1 | 9/2006 | Chotani et al. | |
| 2007/0077232 A1 | 4/2007 | Naughton et al. | |
| 2007/0104023 A1 | 5/2007 | Hood et al. | |
| 2007/0106269 A1 | 5/2007 | Hood et al. | |
| 2007/0149954 A1 | 6/2007 | Hood et al. | |
| 2007/0218133 A1 | 9/2007 | Walker et al. | |
| 2007/0259394 A1 | 11/2007 | Kanome et al. | |
| 2008/0124761 A1 | 5/2008 | Goto et al. | |
| 2009/0104655 A1 | 4/2009 | Buchs et al. | |
| 2009/0190135 A1 | 7/2009 | Clarizia et al. | |
| 2009/0226879 A1 | 9/2009 | Jaffar | |
| 2009/0227027 A1 | 9/2009 | Baker et al. | |
| 2010/0099164 A1 | 4/2010 | Vasala et al. | |
| 2010/0124548 A1 | 5/2010 | Myllylae et al. | |
| 2010/0221301 A1 | 9/2010 | Le et al. | |
| 2010/0221303 A1 | 9/2010 | Le et al. | |
| 2010/0239577 A1 | 9/2010 | Igawa et al. | |
| 2010/0291045 A1 | 11/2010 | Jia et al. | |

(Continued)

FOREIGN PATENT DOCUMENTS

| | | |
|---|---|---|
| CN | 103132163 A | 6/2013 |
| CN | 103374143 A | 10/2013 |

(Continued)

OTHER PUBLICATIONS

Ahmed, E., "Hydrogel: Preperation, Characterization, and Applications: A Review." Journal of Advanced Research, vol. 6, Issue 2, pp. 105-121, Jul. 18, 2013.
Anonymous: "Ethylene-vinyl acetate—Wikipedia", Mar. 22, 2020, XP055679182.
ATCC (Animal Cell Culture Guide: Tips and Techniques for Continuous Cell Lines, 2012).
Buhs, J., "Introduction to Advantages and Problems of Shaken Cultures." Biochemical Engineering Journal, vol. 7, Issue 2, pp. 91-98, Mar. 2001.
Chaplen, F. et al., "Evidence of High Levels of Methylglyoxal in Cultured Chinese Hamster Ovary Cells." Proceedings of the National Academy of Sciences USA: Biochemistry, vol. 95, Issue 10, pp. 5533-5538, Mar. 12, 1998.

(Continued)

*Primary Examiner* — Nghi V Nguyen
(74) *Attorney, Agent, or Firm* — Chandra J. Duncan

(57) ABSTRACT

This disclosure provides a cell culture media extending material capable of releasing nutrients into the cell culture environment slowly overtime. In embodiments, this material is a part of a cell culture vessel. In embodiments, the material is a coating or a film on a surface of a cell culture material. In additional embodiments, the material is a surface upon which cells are cultured, such as a cell culture vessel or a microcarrier.

15 Claims, 12 Drawing Sheets

(56) References Cited

U.S. PATENT DOCUMENTS

| | | |
|---|---|---|
| 2011/0027181 A1 | 2/2011 | Amodei et al. |
| 2011/0053270 A1 | 3/2011 | Chang et al. |
| 2011/0206773 A1 | 8/2011 | Lavik et al. |
| 2011/0229930 A1 | 9/2011 | Menashe |
| 2011/0244573 A1 | 10/2011 | Neubauer et al. |
| 2011/0274742 A1 | 11/2011 | Arinzeh et al. |
| 2012/0003736 A1 | 1/2012 | Stern et al. |
| 2012/0045836 A1 | 2/2012 | Neubauer et al. |
| 2012/0100187 A1* | 4/2012 | Chappa .................. A61L 27/54 427/2.21 |
| 2013/0127653 A1 | 5/2013 | Dienenthal et al. |
| 2013/0244229 A1 | 9/2013 | Bergstrom et al. |
| 2013/0266955 A1 | 10/2013 | Kia et al. |
| 2013/0302307 A1 | 11/2013 | Trumpower et al. |
| 2013/0337562 A1 | 12/2013 | Stern et al. |
| 2014/0024078 A1 | 1/2014 | Gawlitzek et al. |
| 2014/0295545 A1 | 10/2014 | Lin et al. |
| 2015/0147768 A1 | 5/2015 | Chan et al. |
| 2015/0247113 A1* | 9/2015 | Erl ........................ C12M 47/16 422/23 |

FOREIGN PATENT DOCUMENTS

| | | |
|---|---|---|
| EP | 1135105 A2 | 9/2001 |
| EP | 1184123 A1 | 3/2002 |
| EP | 2295533 A2 | 3/2011 |
| JP | 01-282179 A | 11/1989 |
| JP | 09-057291 A | 3/1997 |
| JP | 11-014338 A | 1/1999 |
| JP | 2008-539740 A | 11/2008 |
| JP | 2011-120504 A | 6/2011 |
| JP | 2012-137255 A | 7/2012 |
| JP | 2017-511127 A | 4/2017 |
| JP | 6300450 B2 | 3/2018 |
| KR | 10-2013-0034031 A | 4/2013 |
| WO | 90/08551 A1 | 8/1990 |
| WO | 00/33814 A2 | 6/2000 |
| WO | 02/40413 A1 | 5/2002 |
| WO | 2009/070722 A1 | 6/2009 |
| WO | 2009/070772 A1 | 6/2009 |
| WO | 2011/120498 A1 | 10/2011 |
| WO | 2012/074468 A1 | 6/2012 |
| WO | 2013/040444 A1 | 3/2013 |
| WO | 2014/002192 A1 | 1/2014 |
| WO | 2014/047520 A1 | 3/2014 |
| WO | 2015/148742 A1 | 10/2015 |

OTHER PUBLICATIONS

Chinese Patent Application No. 201580074361.3, Office Action dated May 11, 2021, 8 pages (English Translation Only), Chinese Patent Office.

Chinese Patent Application No. 201580074361.3; English Translation of the First Office Action dated Oct. 9, 2019; China Patent Office; 9 Pgs.

Corning, Incorporated, "Corning glutagro Supplement Frequently Asked Questions." Pod CLS-CG-FQ-008 Rev 1, pp. 1-2, Aug. 2012.

Cruz H J et al: "Metabolically optimised BHK cell fed-batch cultures", Journal of Biotechnology, Elsevier Science Publishers, Amsterdam, NL, vol. 80, No. 2, Jun. 23, 2000 (Jun. 23, 2000), pp. 109-118, XP004213500.

Eigenbrodt, E. et al., "New Perspectives on Carbohydrate Metabolism in Tumor Cells." Regulation of Carbohydrate Metabolism vol. II, Chapter 6, pp. 141-179, 1985.

European Patent Application No. 21163819.2 European search report dated Jul. 21, 2021; 7 pages; European Patent Office.

Gryseels, T., "Considering Cell Culture Automation in Upstream Bioprocess Development." BioProcess International, vol. 6, pp. 12-16, Dec. 1, 2008.

Hedge, S. et al., "Controlled Release of Nutrients to Mammalian Cell Cultured in Shake Flasks." Biotechnology Progress, vol. 28, No. 1, pp. 188-195, Oct. 14, 2011.

International Search Report and Written Opinion of the International Searching Authority; PCT/US2015/061740; dated Apr. 13, 2016; 17 Pages; European Patent Office.

Japanese Patent Application No. 2017-527893, Decision to Grant dated Oct. 5, 2021, 5 pages (2 pages of English Translation and 3 pages of Original Document), Japanese Patent Office.

Japanese Patent Application No. 2017527893; Machine Translation of the Office Action dated Oct. 2, 2019; Japan Patent Office; 8 Pgs.

Jeude, M. et ai., "Fed-Batch Mode in Shake FlasKs by Slow-Release Technique." Biotechnology and Bioengineering, vol. 95, No. 3, pp. 433-445, May 30, 2006.

Lee, Y. et al., "Low-Glutamine Fed-Batch Cultures of 293-HEK Serum-Free Suspension Cells for Adenovirus Production." Biotechnology Progress, vol. 19, pp. 501-509, Jan. 4, 2003.

Legmann, R. et al., "A Predictive High-Throughput Scale-Down Model of Monoclonal Antibody Production in CHO Cells." Biotechnology and Bioengineering, vol. 104, No. 6, pp. 1107-1120, Jul. 21, 2009.

Mei et al., "Handbook for China Licensed Pharmacist", In Hu Bei science and technology Press, 2002, p. 452. (1 page of English Translation and 4 pages of original document).

Panula-Perala, J. et al., "Enzyme Controlled Glucose Auto-Delivery for High Cell Density Cultivations in Microplates and Shake Flasks." Microbial Cell Factories, vol. 7, Issue 31, pp. 1-12, Nov. 18, 2008.

Roy, B. et al., "Toxic Concentrations of Exogenously Supplied Methylglyoxal in Hybridoma Cell Culture." Cytotechnology, vol. 46, pp. 97-107, Oct. 2004.

Shin S-C et al: "Controlled release of triprolidine using ethylene-vinyl acetate membrane and matrix systems", Eur. J. Pharmaceut. Biopharmaceut., vol. 54, No. 2, Sep. 1, 2002, pp. 201-206, XP004377364.

Thomas, D. et al., "A Novel Automated Approach to Enabling High-Thoughput Cell Line Development, Selection, and Other Cell Culture Tasks Performed in Erlenmeyer (Shake) Flasks." Journal of the Association for Laboratory Automation, vol. 13, pp. 145-151, Jun. 1, 2008.

Weichang Zhou et al.: "Alteration of mammalian cell metabolism by dynamic nutrient feeding", Cytotechnology, Kluwer Academic Pub Li Shers, DO, vol. 24, No. 2, Jun. 1, 1997 (Jun. 1, 1997), pp. 99-108, XP019236475.

Wikipedia, "Ethylene-vinyl acetate", Accessed Mar. 22, 2020, 4 pgs. retrieved from: https://en.wikipedia.org/wiki/ethylene-vinyl_acetate.

Wong, D. et al., "Impact of Dynamic Online Fed-Batch Strategies on Metabolism, Productivity an N-Glycosylation Quality in CHO Cell Cultures," Biotechnology and Bioengineering, vol. 89, No. 2, pp. 164-177, Dec. 8, 2004.

Yuk, I. et al., "Controlling Glycation of Recombinant Antibody in Fed-Batch Cell Cultures." Biotechnology and Bioengineering, vol. 108, No. 11, pp. 2600-2610, May 26, 2011.

Zhou, W. et al., "Alteration of mammalian cell metabolism by dynamic nutrient feeding." Cytotechnology, vol. 24, pp. 99-108, Jul. 1997.

Zhou, W. et al., "High Viable Cell Concentration Fed-Batch Cultures of Hybridoma Cells Through On-line Nutrient Feeding." Biotechnology and Bioengineering, vol. 46, No. 6, pp. 579-587, Jun. 1995.

* cited by examiner

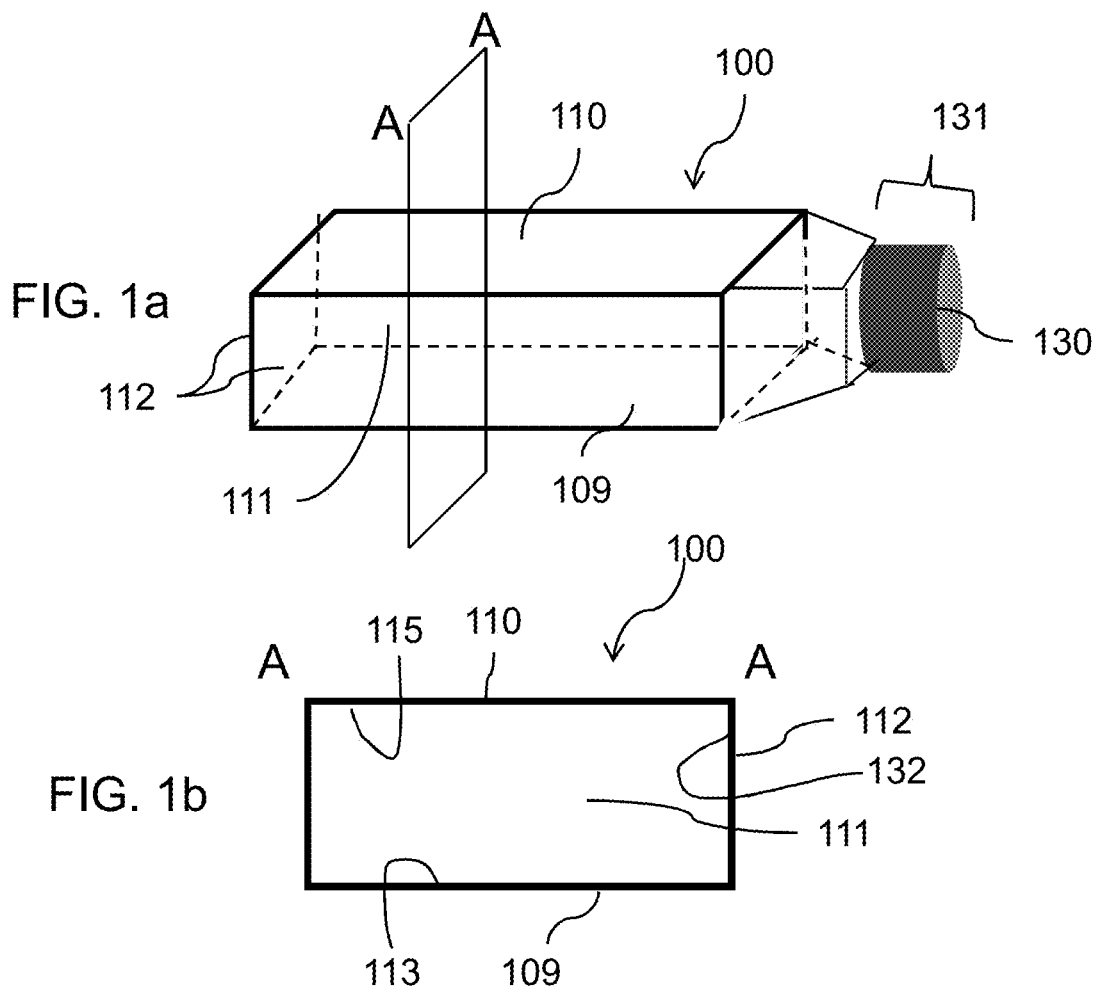
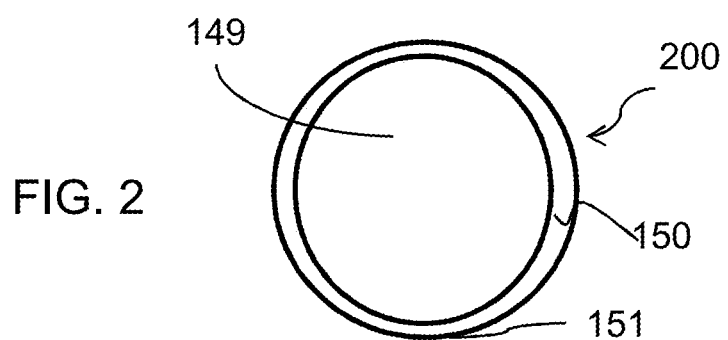

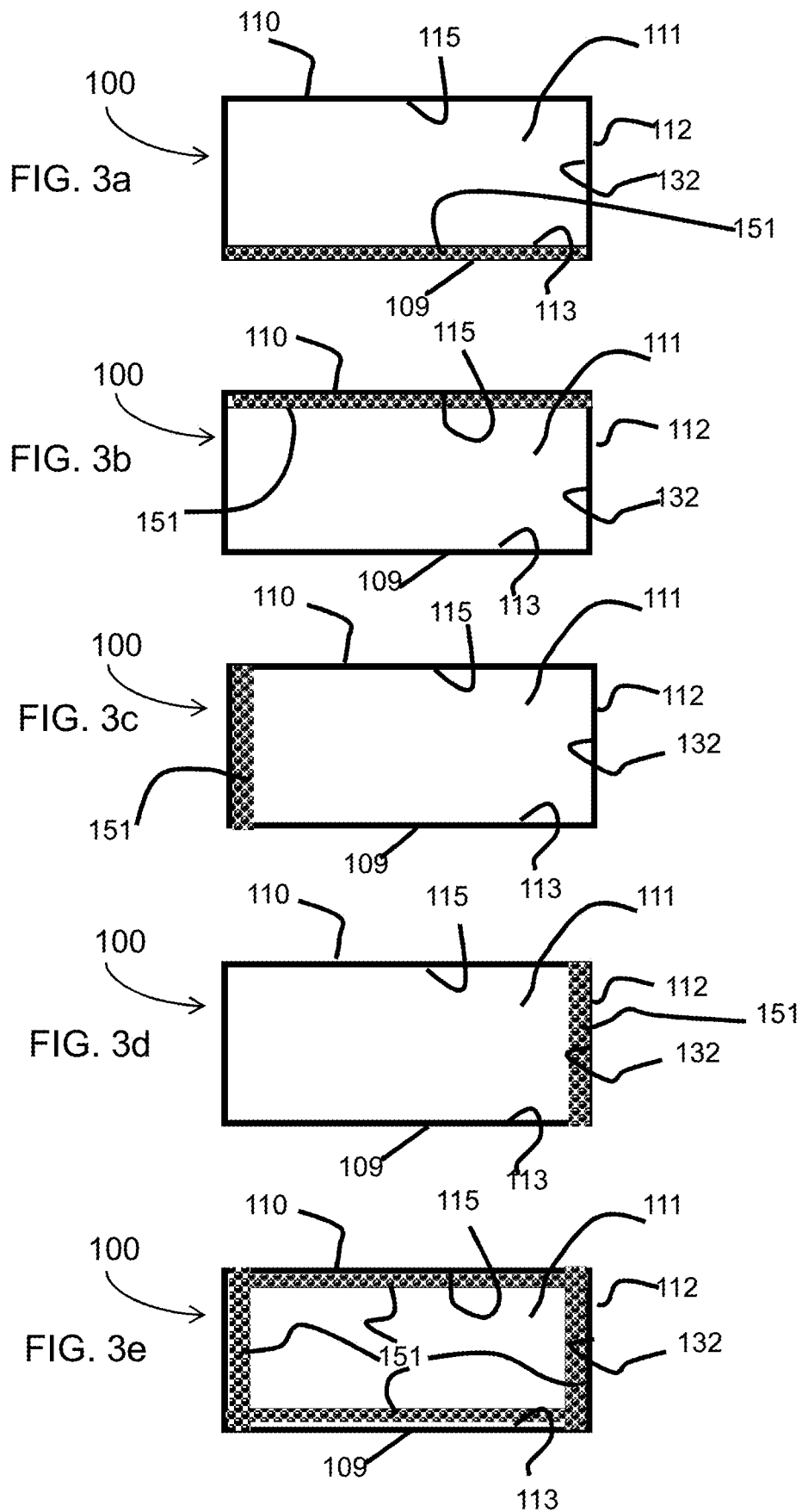

CELL CULTURE MEDIA EXTENDING MATERIALS AND METHODS

This application is a continuation of U.S. patent application Ser. No. 15/528,644 filed on May 22, 2017, which is a national stage application under 35 U.S.C. § 371 of International Application No. PCT/US2015/061740, filed on Nov. 20, 2015, which claims the benefit of priority under 35 U.S.C. § 119 of U.S. Provisional Application Ser. No. 62/084,356 filed on Nov. 25, 2014, the content of which are relied upon and incorporated herein by reference in their entirety.

BACKGROUND

In cell culture systems, nutrients that cells require to survive in culture are present in liquid media that bathes cells. To maintain cells in static culture for a long period of time, concentrations of nutrients sufficient to feed cells over that long period of time are provided in the media. However, nutrients break down over time. For example, glutamine, an essential amino acid, and glucose, necessary for energy metabolism, are provided in cell culture media. These nutrients degrade over time. The breakdown of these nutrients can be affected by the concentration of the nutrients themselves. Breakdown products of nutrients such as glutamine and glucose can be toxic to cells. Therefore, providing relatively high concentrations of nutrients in cell culture media in order to extend the life of cell culture may result in media which becomes toxic to cells as nutrients break down over time. These effects may limit the lifespan of cell culture.

The disclosure relates to materials useful for the sustained and controlled delivery of nutrients to cultured cells in order to provide environments suitable for extending the duration of cell culture.

SUMMARY

The disclosure provides a surface, exposed to cell culture, having media extending materials which have sequestered or captured cell culture nutrients and provide a mechanism for the release of nutrients in a controlled and sustained way which support cells in culture for a longer time. In embodiments the media extending materials are coatings or films, applied to a cell culture surface, which are capable of releasing cell culture nutrients over time. In embodiments the media extending materials disclosed herein are polymers which swell to less than 50% water by weight in an aqueous environment, which are mixed with nutrients, or have captured nutrients, or contain nutrients. In embodiments, nutrients are captured or sequestered in polymer in crystalline or solid form.

In additional embodiments, the disclosure provides methods of culturing cells in the presence of a cell culture surface having media extending materials where the nutrients, captured in a polymer matrix, dissolve in the presence of aqueous media, and are slowly released into the media. When the nutrients dissolve in an aqueous environment, an osmotic pump may be created in pockets in the polymer matrix, allowing nutrients to flow from the more concentrated environment of the polymer pocket, into the media. This sequestration of nutrients in the polymer matrix allows for the slow introduction of nutrients into media without opening a cell culture vessel. This sequestration also allows cells to be cultured, in static culture or in dynamic culture conditions, in the presence of lower concentrations of nutrients which, in higher concentrations, may be toxic to cells, directly or indirectly.

In embodiments, the disclosure provides a cell culture vessel having a surface comprising a cell culture media extending material. In embodiments, the cell culture extending material can be a coating or a film, or a coating which is a film. In embodiments, the cell culture media extending material comprises a hygroscopic polymer comprising at least one sequestered nutrient. In embodiments, the cell culture vessel comprises at least one cell culture compartment, each cell culture compartment comprising a bed, a ceiling and at least one wall. In embodiments the cell culture media extending material is on a bed, a ceiling or a wall of a cell culture compartment, or a combination of the bed, the ceiling or the wall.

In embodiments, the disclosure provides a cell culture media extending material comprising a hygroscopic polymer and at least one nutrient. In embodiments, the cell culture media extending material forms part of a cell culture vessel or part of a microcarrier. In embodiments, the hygroscopic polymer comprises EVA and the at least one nutrient is glucose, glutamine or a combination of glucose and glutamine.

In embodiments, the disclosure provides a method of culturing cells including: (a) introducing cells into a cell culture chamber comprising a cell culture media extending material, wherein the cell culture media extending material comprises a hygroscopic polymer comprising at least one sequestered nutrient; (b) incubating the cells in static culture in the presence of media having an L-glutamine concentration less than 2 mM. In embodiments, the glutamine concentration is between 0 and 1.5 mM.

BRIEF DESCRIPTION OF THE DRAWINGS

In embodiments of the disclosure:

FIGS. 1a and 1b are illustrations of a cell culture vessel in an embodiment. FIG. 1b is a cross-section of the cell culture vessel shown in FIG. 1a, taken at plane A-A shown in FIG. 1a.

FIG. 2 is an illustration of a cell culture surface in the form of a microcarrier, in another embodiment.

FIGS. 3a-3e are cross-sections of a cell culture vessel taken at plane A-A shown in FIG. 1B, showing embodiments of the material on interior surfaces of a cell culture vessel.

DETAILED DESCRIPTION

Figure 4A:
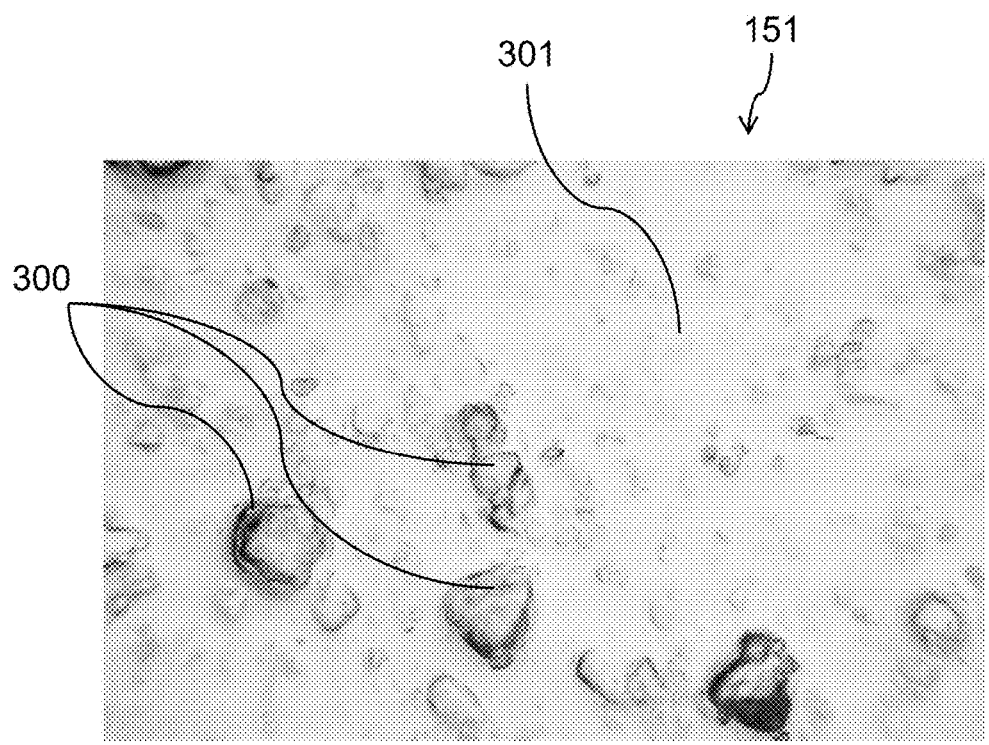
FIGS. 4a and 4b are images of embodiments of cell culture extending materials, in the absence (FIG. 4a) and in the presence (FIG. 4b) of dPBS.

In embodiments, this disclosure provides a cell culture media extending material capable of releasing nutrients into a cell culture environment slowly over time. In additional embodiments, the material is exposed to cell culture media. In embodiments, this material is a part of a cell culture vessel. In embodiments, the material is a coating or a film on a surface of a cell culture material. In additional embodiments, the material is a surface upon which cells are cultured, such as a cell culture vessel or a microcarrier.

In embodiments, the disclosed cell culture media extending material, and the disclosed method of making and using the cell culture media extending material, provide one or more advantageous features or aspects, including for example those discussed below. Features or aspects recited in any of the claims are generally applicable to all facets of the invention. Any recited single or multiple feature or aspect in any one claim can be combined or permuted with any other recited feature or aspect in any other claim or claims.

DEFINITIONS

"Nutrient" refers to any compound or component, whether of chemical or biological origin, that can be used in the disclosed material, which is contacted with cell culture media to maintain or promote the growth or proliferation of cells, or cellular production of biologically active substances. "Component," "nutrient," "sustenant," or "ingredient" can be used interchangeably and all refer to such compounds. Nutrients that can be used in cell culture media can include, for example, amino acids, salts, metals, sugars, lipids, nucleic acids, hormones, vitamins, fatty acids, proteins, and like sub stances, or combinations thereof. Other ingredients that can promote or maintain cultivation of cells in vitro (e.g., in cell culture) can be selected by those of skill in the art, in accordance with a particular need.

"Material" means the cell culture media extending material disclosed herein, in embodiments.

"Sequestered" means a nutrient, in solid or crystalline form, that is captured in or mixed in a polymer matrix. Nutrients that are trapped beneath a layer of polymer or trapped between layers of polymer are also "sequestered".

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The material, and the method of making and using the material of the disclosure can include the components or steps listed in the claims, plus other components or steps that do not materially affect the basic and novel properties of the materials, or methods of making and use, such as a particular apparatus or vessel configuration, particular additives or ingredients, a particular agent, a particular structural material or component, a particular incubation or culture condition, or like structure, material, or process variable selected.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for compositions, ingredients, additives, dimensions, conditions, and like aspects, and ranges thereof, are for illustration only; they do not exclude other defined values or other values within defined ranges. The compositions and methods of the disclosure can include any value or any combination of the values, specific values, more specific values, and preferred values described herein, including explicit or implicit intermediate values and ranges.

Successful culturing of cells requires consideration of nutrient consumption and metabolic waste accumulation. Cells in culture typically grow in an aqueous media environment. Cells can be grown in static culture, in perfusion culture, or in mixed or shaken culture. Cells cultured in static culture conditions, conditions that do not have a constant flow of nutrient media in or through the cell culture vessel, sit in cell culture media for extended periods of time. Nutrients, provided by the cell culture media, are used up by the cultured cells over time, and byproducts, or waste products, build up. These waste products may be toxic.

Cell culture media contains vital amino acids, sugars, salts, growth factors, and other ingredients important for maintaining the health of cells in culture. One important amino acid ingredient in cell culture media is glutamine. Glutamine decomposes spontaneously in cell culture media over time. Cell culture medium is normally formulated with excessive glutamine to compensate for its decomposition. However, ammonium is produced by to the spontaneous decomposition of L-glutamine.

Ammonium is also produced as a result of cell metabolism. Too much ammonium in cell culture media may be toxic to cells in culture. It has been demonstrated that fed-batch systems benefit from use of low sustained glutamine concentration to reduce the rate of ammonium formation. This has been achieved via frequent or continuous feeding which increases the volume of media required and dilutes culture products formed.

Cell culture media can be, for example, aqueous-based and can comprise a number of ingredients in a solution of, for example, deionized, distilled water to form a "basal media." Any basal medium can be used in accordance with the disclosed methods. The basal media can include, for example, one or more of the following ingredients: amino acids, vitamins, organic salts, inorganic salts, trace elements, buffering salts, and sugars. Preferably, the basal media can include, for example, one or more amino acids, one or more vitamins, one or more inorganic salts, adenine sulfate, ATP, one or more trace elements, deoxyribose, ethanolamine, D-glucose, glutathione, N-[2-hydroxyethyl]-piperazine-N'-[2-ethanesulfonic acid] (HEPES), or one or more other zwitterion buffers, hypoxanthine, linoleic acid, lipoid acid, insulin, phenol red, phosphoethanolamine, putrescine, sodium pyruvate, thymidine, uracil, and xanthine. These ingredients are commercially available.

Amino acid ingredients that can be included in the culture media of the disclosure can include, for example, L-alanine, L-arginine, L-asparagine, L-aspartic acid, L-cystine, L-cysteine, L-glutamic acid, L-glutamine, glycine; L-histidine, L-isolcucine, L-leucine, L-lysine, L-methionine, L-phenylalanine, L-proline, L-serine, L-threonine, L-tryptophan, L-tyrosine, and L-valine.

Vitamin ingredients that can be included in the media of the disclosure can include, for example, ascorbic acid magnesium salt, biotin, choline chloride; D-Ca$^{++}$ pantothenate, folic acid, i-inositol, menadione, niacinamide, nicotinic acid, paraminobenzoic acid (PABA), pyridoxal, pyridoxine, riboflavin, thiamine-HCl, vitamin A acetate, vitamin $B_{12}$ and vitamin $D_2$.

Inorganic salt ingredients that can be used in the media of the disclosure can include, for example, $CaCl_2$, KCl, $MgCl_2$, $MgSO_4$, NaCl, $NaHCO_3$, $Na_2HPO_4$, $NaH_2PO_4H_2O$, and ferric citrate chelate or ferrous sulfate chelate.

Trace elements that can be used in the media of the disclosure can include, for example, ions of barium, bromium, cobalt, iodine, manganese, chromium, copper, nickel, selenium, vanadium, titanium, germanium, molybdenum, silicon, iron, fluorine, silver, rubidium, tin, zirconium, cadmium, zinc and aluminum. These ions can be provided, for example, in trace element salts.

Additional ingredients that can optionally be included in the media are, for example, growth factors, insulin (especially as insulin-Zn$^{++}$) and transferrin. These additional ingredients can be formulated into the media at the typical biologic or physiologic concentrations. An iron salt or chelate (e.g., ferric citrate chelate or ferrous sulfate) can be used in the media as a substitute for transferrin. Recombinant insulin or zinc based salts (e.g., ZnCl, etc.) can be substituted for animal- or human-derived insulin.

Many strategies have been employed to maximize the duration of cell culture, while maintaining the health of cells in culture. For example, frequent media changes, the introduction of nutrient-releasing materials into the media, perfusion culture and fed-batch processes have been used.

In order to maximize cell culture nutrients in the media, and minimize waste product build-up, media may be changed. Old media (which may be depleted in nutrients and contain waste products) is removed and fresh media is delivered to cells in culture. However, when media is changed, there is risk that the cell culture may be compromised. For example, when cell culture vessels are opened to remove old media and deliver new media, contamination may occur. Media changes also require the time and attention of cell culture professionals. That is, media changes have contamination risk and labor costs.

Efforts have been made to extend the time between media changes, in order to reduce labor costs and reduce the risk of contamination during media changes. For example, cell culture media may contain an overabundance of necessary nutrients, in order to ensure that sufficient nutrients are present in cell culture for a longer period of time, as the cells use up the nutrients. This results in media which is overly rich in certain nutrients such as, for example, glutamine or glucose. Glutamine (also referred to herein interchangeably as "L-glutamine") hydrolyzes in an aqueous environment leading to the production of ammonium. Glutamine is also broken down by cells to produce ammonium. However, the production of ammonium from cellular metabolism of glutamine may contribute less to an accumulation of ammonium in media than the hydrolysis of glutamine in an aqueous environment. Glucose is broken down by cells form lactic acid. In a well-oxygenated cell culture system, the creation of lactic acid is a result of an overabundance of glucose. Ammonium and lactic acid can build up and can be toxic to the cells. So, by providing media with an overabundance of these compounds, in an effort to provide sufficient nutrients to sustain cells in culture for an extended period of time, it is paradoxically possible that cells find themselves in a less healthy environment than is necessary, as toxic by-products build up in the media over time.

Techniques have been developed to slowly release nutrients such as glucose into cell culture media by providing slow-release glucose. For example U.S. Pat. No. 3,926,723 discloses a method of culturing cells which includes providing a media which includes an enzymatically-releasable glucosyl moiety (starch) and an enzyme capable of releasing the glucosyl moiety (for example maltase and amylase) into cell culture media by enzymatically releasing glucose from the starch polymer. Starch breaks down, in the presence of the enzymes, to form glucose.

Published U.S. Patent Application 2011/0244573 discloses pellets or pills which can added to cell culture, along with enzymes to release nutrients from the structure of the pellet for fed-batch cultivation of cell culture. Starch tablets with a lactose core were disclosed for *E. coli* cultivation. Lactose acted to degrade the starch of the tablet to provide glucose to the cell culture.

Cells can also be grown in perfusion culture conditions. However, perfusion cell culture systems require significant equipment including pumps, tubing and connectors, to ensure that fresh media is consistently delivered to the cells in culture, while maintaining sterility and avoiding unnecessary disruption of the cells. For example, international patent publication WO2013/04044 entitled "Pre-Programmed Non-Feedback Controlled Continuous Feeding of Cell Cultures" discloses an apparatus for providing continuous feed streams to a cell culture.

Other strategies include fed-batch or batch-fed processes that supply feed concentrates to cell cultures. However, fed-batch, or bolus feeding, results in variability in the concentration of nutrients in a cell culture over time, and can be labor intensive.

In static culture, products like Glutagro™, available from Corning, Incorporated, Corning, N.Y., or GlutaMAX™, available from Life Technologies, Carlesbad, Calif., are sometimes used. These products are cell culture media additives which contain glutamine dipeptides (L-alanyl-L-glutamine dipeptides) which slowly break down to release glutamine. This leads to much lower ammonium build up in the media in cell culture, but it also releases alanine which causes some cell types to perform poorly. Mammalian cell culture technologies are widely used in biomedical research and pharmaceutical industries. Recombinant protein production in mammalian cells is typically carried out using suspension-adapted cells for ease of scale up. Modern cell cultivation on a laboratory scale is mainly based on shaken cultures which are generally performed as batch cultures, i.e., nutrients are added at the start of cultivation. Compared to industrial fed-batch processes, the shaken cultures are characterized by low volumetric cell and product yields. Shaken flasks provide only limited information for bioprocess development; culture parameters are often re-optimized in fed batch modes and this significantly increases time and labor costs. In contrast to variable shaking cultures, in well controlled bioreactor scale cultivations, the fed-batch technology is mostly applied since it provides better process control for nutrient and metabolite concentrations, oxygen level, biomass density, and media pH. Lack of process control capabilities in batch cultures is the main reason that process and media optimization results performed in batch mode cannot be directly translated into larger scale production in fed-batch operation mode. To overcome these issues miniature bioreactors or automation technologies (see for example, Legmann, R., et al., A predictive high-throughput scale-down model of monoclonal antibody production in CHO cells. *Biotechnol Bioeng*, 2009; 104; 1107-1120; Thomas, D., et al., A novel automated approach to enabling high-throughput cell line development, selection, and other cell culture tasks performed in Erlenmeyer (shake) flasks, *J. Assoc. Lab Autom.*, 2008; 13: 145-151; Gryseels, T., Considering cell culture automation in upstream bioprocess development, *Bioproc. Intl.*, 2008; 6: 12-16), are used to allow high throughput, fed-batch operation with automated feeding and control of pH. Because these technologies are expensive, shaker flasks continue to be widely used as the main scale down platform across industry and academia in process development for mammalian cells (see Buhs, J., Introduction to advantages and problems of shaken cultures, *Biochem. Eng. J.*, 2001; 7: 91-98).

A major challenge is not only the adaptation of the fed-batch principle in the small scale, which is mostly done by intermittent feeding, but more importantly reaching high cell densities at the same time. In batch process, cell density is determined by the concentration of growth limiting nutrient source, media pH, and toxic metabolite concentrations. This creates a dilemma: high cell densities are only obtained when enough glucose is available as carbon source. At the same time, bolus additions of glucose can cause large transient increases in nutrient concentration, which can lead to high osmolarity and high waste metabolite concentrations, e.g., high glucose concentrations can lead to an increase in lactate production and pH decrease (see Zhou, W. C., et al., High viable cell concentration fed batch cultures of hybridoma cells through online nutrient feeding, *Biotechnol Bioeng.*, 1995; 46: 579-587; Chee, F. W. D., et al., Impact of dynamic online fed-batch strategies on metabolism, productivity an N-glycosylation quality in CHO cell cultures, *Biotechnol. Bioeng*, 2005; 89: 164-177). In addition, glycation of a recombinant antibody could be controlled by controlling glucose concentrations to low levels in the media (see Yuk, I. H., et al., Controlling glycation of recombinant antibody in fed-batch cell cultures, *Biotechnol. Bioeng*, 2011; 108; 2600-2610). The main pathway of glucose utilization by the cells is glycolysis. Tumor derived cell lines generally lose the ability to control glycolytic flux on the basis of energy needs (see Eigenbrodt, E., et al., New perspectives on carbohydrate metabolism in tumor cells, R. Brietner (ed.), Regulation of Carbohydrate Metabolism, Vol. 2., CRC Press, Boca Raton, Fla.). As a result, glycolysis is controlled by the concentration of glucose in the extracellular growth medium. In a batch cell culture, glucose is often present at significantly higher concentrations (up to 50 mM) than found in the blood stream (5 mM or less). It has been demonstrated that decreases in CHO (Chinese hamster ovary) cell viability is caused by high levels of toxic metabolite methylglyoxal, which is produced as a by-product of glycolysis at high glucose concentrations (see Chaplen, F. W. R., et al., Evidence of high levels of methylglyoxal in cultured Chinese hamster ovary cells, Proc. Natl. Acad. Sci. USA, 1998; 95:5533-5538; Roy, B. M., et al., Toxic concentrations of methylglyoxal in hybridoma cells culture, *Cytotechnology*, 2005; 46: 97-107).

To solve or mitigate these problems caused by high glucose concentration in cell culture media there is a growing need for continuous substrate delivery source for high density cultivations. One example for microorganism culture is EnBase™, an enzyme controlled glucose delivery system that was developed and is now commercially available to culture microorganisms (see Panula-Perala, J., et al., Enzyme controlled glucose auto-delivery for high cell density cultivations in microplates and shake flasks, *Microbial Cell factories*, 2008; 7:31). EnBase™ uses glucoamylase/starch as a carbon source for the generation of glucose. Use of glucoamylase in cell culture media imposes limitations for mammalian cells. Alternatively, glucose embedded into polydimethylsiloxane resin has been used as a slow release technique for culture of *H. polymorpha* in shaker flasks (see Jeude, M., et al., Fed-Batch Mode in Shake Flasks by Slow-Release Technique, *Biotechnology and Bioengineering*, 2006; 95; commercially available as FeedBeads at kuhner.com). From the literature it is known that PDMS has high nonspecific binding capacity toward the proteins in cell culture media and as such is not desirable for mammalian cell culture applications. However, the use of a hydrogel based glucose delivery system has been developed for the mammalian cell culture (see Hedge, S., et al., Controlled release of nutrients to mammalian cell culture in shake flasks, *Biotechnol. Prog.*, 2012; 28: 1). This system is based on HEMA:EGDMA hydrogel disk with encapsulated glucose powder. Because of unreacted residual monomers such system requires extensive washing of hydrogels to mitigate cellular toxicity.

U.S. Pat. No. 8,563,066, to Sexton, et al., issued Oct. 22, 2013, entitled "Sustained Release of Nutrients In Vivo," mentions nutritional compositions delivered in vivo in a time controlled manner sustainable over long periods of time, provide enhanced athletic performance, increased hand/eye coordination, and concentration on the task at hand. The compositions can include an aqueous suspension, comprising (a) one or more nutritional supplements; and, (b) one or more hydrogel microparticles that encapsulate one or more nutritional supplements of (a), wherein the one or more hydrogel microparticles (i) have a diameter between 1 to 1000 micrometers; (ii) comprise one or more compounds that are non-toxic, crosslinked, and that release the encapsulated one or more nutritional supplements in a time controlled and sustained manner in vivo; (iii) are pH-sensitive, wherein one or more compounds of the hydrogel microparticles do not swell at pH 1-3; and (iv) are temperature-sensitive, wherein one or more compounds of the hydrogel microparticles have a lower critical solution temperature in aqueous solution. The one or more compounds in (b)(ii) for the time controlled and sustained release of the nutritional supplements can be biodegradable polymers, bioadhesives, binders, or a combination. The biodegradable polymers and binders can be one or more of poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, polysaccharides and polysaccharide copolymers with polyethers. Sexton also mentions that the microspheres can contain a mixture of nutritional compounds and the microsphere is composed of a biodegradable material that is released over a certain period of time. For example, in order to provide an initial burst of nutrients to provide an immediate reservoir of energy or nutrients to the individual, the nutritional compounds are formulated as such and can contain a variety of carbohydrates, amino acids, electrolytes, vitamins, etc. in differing ratios. The second group can contain a differing ratio of carbohydrates:amino acids:vitamins, etc., or strictly different or similar carbohydrates that are released over a longer period of time to maintain a sustainable release of the nutrients. The formulation of the nutrients in the microspheres and the timing of release can be varied depending on the types of activity, the individual, age, weight and nutritional needs. For example, a marathon runner (sustained nutrition over long period) would have different nutritional needs to a sprinter (burst of nutrition).

As a general matter, products of biodegradation are generally undesirable in in vitro or ex vivo cell culture. In embodiments, the material polymers selected for use in the present disclosure are not readily biodegradable in situ (i.e., within and during the cell culture).

U.S. Pat. Publication 20090190135, entitled "Cell Culture Hydrogel With pH Indicator," mentions devices, compositions and methods for maintaining conditions in a cell culture and for measurement of conditions in the cell culture. In particular, the invention provides hydrogel materials, apparatus and methods for several non-invasive techniques of maintaining glucose and pH levels in cell cultures at near-optimal levels and the non-invasive measurement of pH levels in cell cultures.

This disclosure provides embodiments of a material to release glutamine and other nutrients, including glucose, in a steady, controlled manner, which allows for more robust cell culture conditions for longer periods of time. In addition, this improved material creates conditions which allow the media in cell culture to contain significantly less glucose and glutamine, while still supporting superior cell growth and reduced ammonium and lactate production. This allows for longer cell culture without requiring media changes (also known as "refeeding") while reducing the risk of contamination and increased labor costs that frequent media changes bring. Extending media's capacity to support cells also may enable higher cell densities in vessels, which would also make cell culture more efficient.

Figure 5:
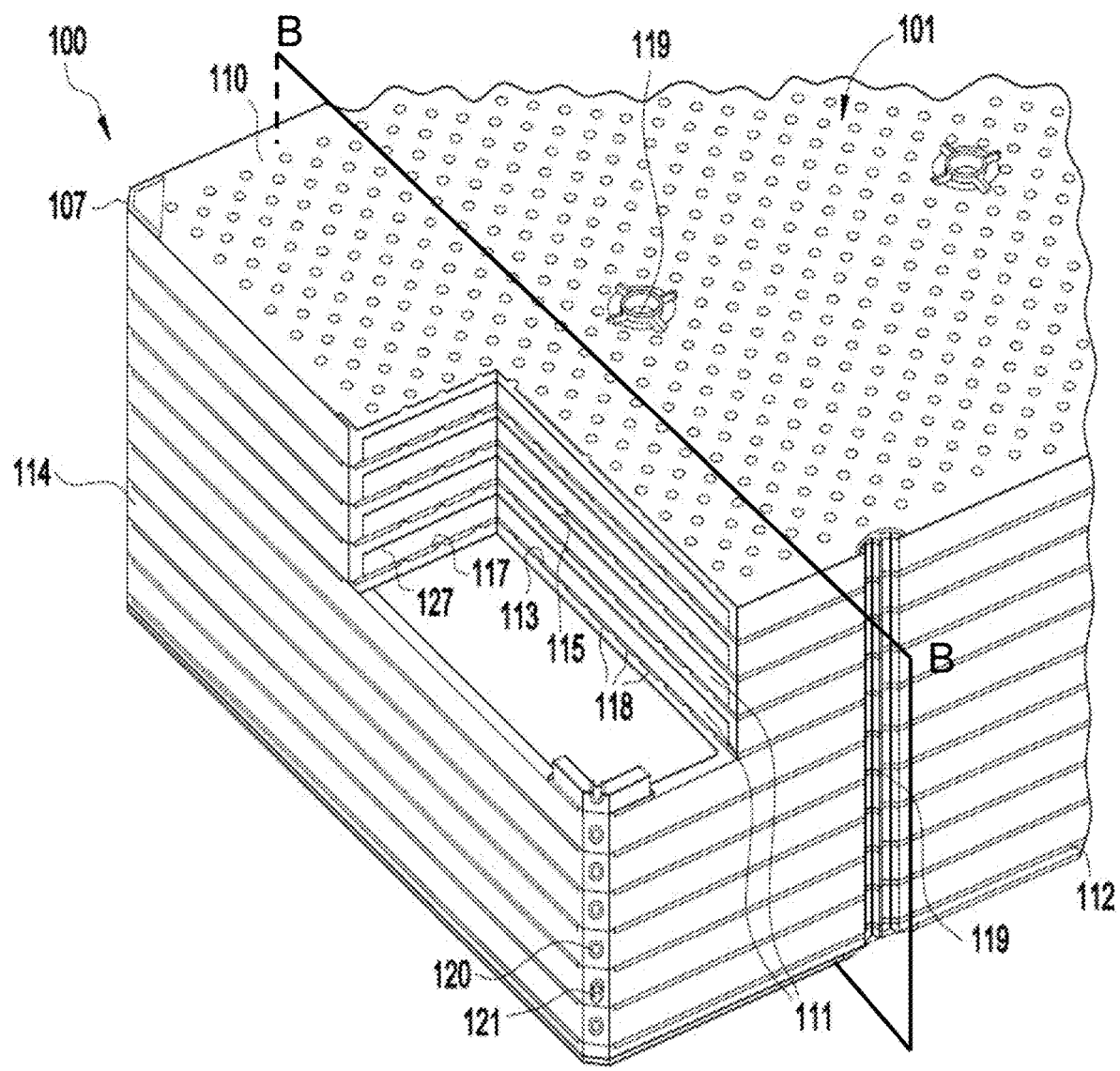
FIG. 5 is a partial cut-away illustration of a multi-layer cell culture vessel, in another embodiment.
Figure 6:
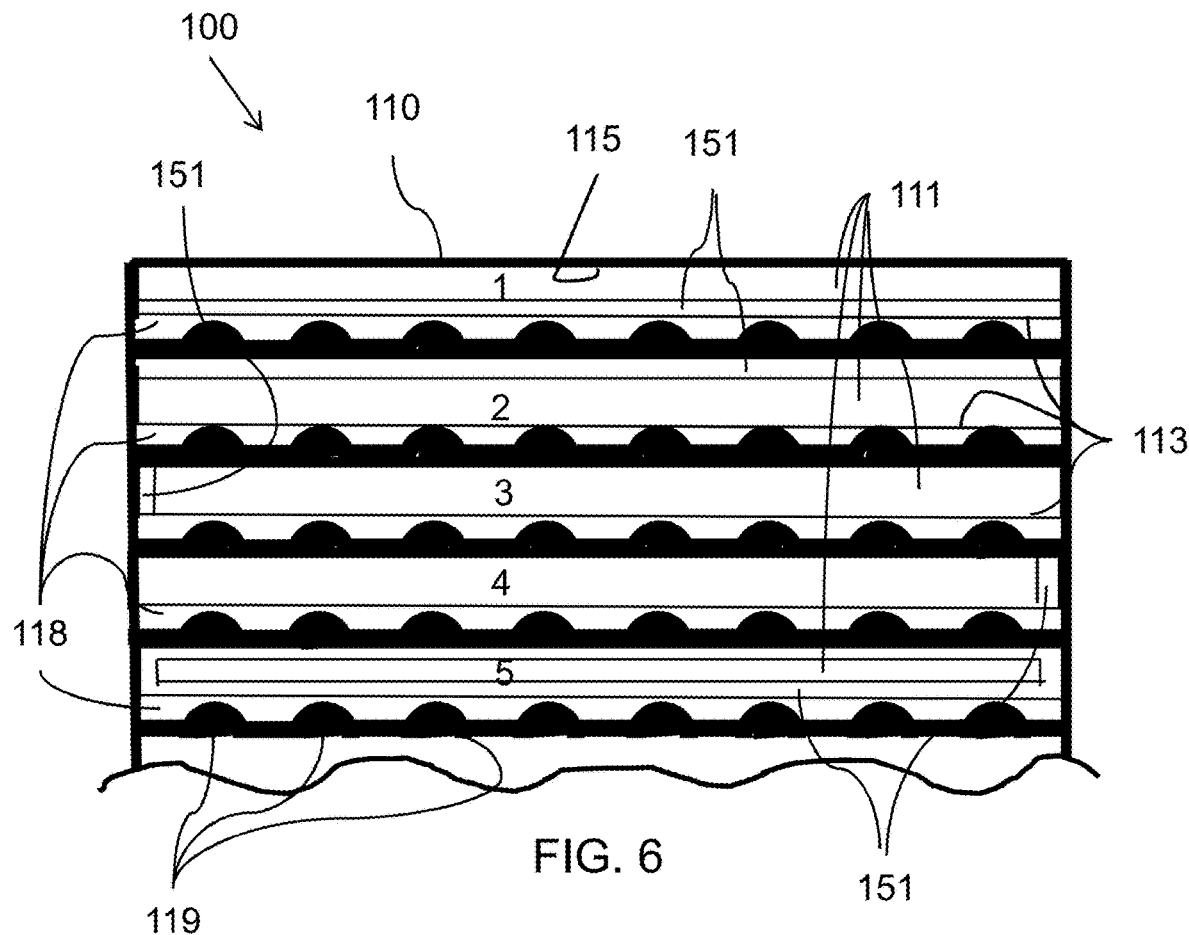
FIG. 6 is a cross-section of a cell culture vessel, taken at plane B-B shown in FIG. 5, showing five (5) embodiments of the material on interior surfaces of a multi-layer cell culture vessel.

FIGS. 1a and 1b are illustrations of a cell culture vessel 100 in an embodiment. The vessel (shown here as a flask, but the cell culture vessel may be any shape suitable for cell culture, including a petri dish, a flask, a multi-well plate, a bag, a bioreactor, a multi-layer container, a multi-layer flask (as shown in FIG. 5 and FIG. 6, in an embodiment), a bed, a microcarrier (as shown in FIG. 2) or any other container, vessel, flask, or surface suitable for cell culture. The cell culture vessel or surface may be suitable to support adherent or non-adherent cells, animal cells, yeast cells, insect cells, eukaryotic cells, prokaryotic cells, tissue culture, organ culture, plant culture, primary cells, cell lines, genetically engineered cells or organisms, or any other cell culture purpose.

In the embodiment shown in FIGS. 1a and 1b, the vessel 100 has a bottom 109, a top 110, side walls 112, and a necked opening 131, shown in FIG. 1a with a cap 130 attached to the necked opening. The inside of the vessel shown in FIG. 1a is a cell culture chamber 111. FIG. 1b is a cross-section of the cell culture vessel shown in FIG. 1a, taken at plane A-A shown in FIG. 1a. As shown in FIG. 1B, the vessel 100 has interior surfaces. The top wall 110 has an interior surface 115, also called a ceiling 115. The bottom wall 109 has an interior surface 113, also called a bed 113. Each side wall 112 has an interior surface 132.

FIG. 2 is a microcarrier embodiment. FIG. 2 shows a microcarrier 200 in cross-section. The microcarrier has a microcarrier body 149 which has a microcarrier surface 150. Material 151 is shown in a layer on the microcarrier surface 150.

FIG. 3 a-e are illustrations of cross-sections of a cell culture vessel, taken at plane A-A shown in FIG. 1B, showing embodiments of material on interior surfaces of a cell culture vessel. In each of FIGS. 3a-3e, a cross-section of the cell culture vessel 100 in the embodiment shown in FIGS. 1a and 1b is shown. The cell culture vessel 100 has a top wall 110 having an interior top surface 115 or ceiling 115, side walls 112 having interior side wall surfaces 132, a bottom wall 109 having an interior bottom surface 113 or bed 113 and a cell culture chamber 111. In FIG. 3a, material 151 is shown on the interior surface 113 or bed 113 of bottom wall 109. In FIG. 3b, material 151 is shown on the interior surface 115 of top wall 110, or ceiling 115. In FIG. 3c, material 151 is shown on the interior surface 132 of side wall 112. In FIG. 3d, material 151 is shown on the interior surface 132 of the opposite side wall 112. In FIG. 3e, material 151 is shown on the interior surfaces 115, 113, and 112 of each of top wall 110, bottom wall 109 and side walls 112. Although FIG. 3e shows material on each of the interior surfaces of the cell culture chamber 115, 113, and 112 of each of top wall 110, bottom wall 109 and side walls 112, material may be present on one, more than one, but less than all, or all of the interior surfaces 115, 113, and 112 of each of top wall 110, bottom wall 109 and side walls 112.

In embodiments, material 151 may completely cover a surface, or may partially cover a surface. In embodiments, material 151 is a coating applied to one or more of interior surfaces 115, 113, and 112 of each of top wall 110, bottom wall 109 and side walls 112. A coating may be applied with wet chemistry by methods such as cast and cure. That is, a solution of material may be introduced into vessel 100 and allowed to coat one or more of internal surfaces of vessel. Additional steps may be taken, such as a curing step or a drying step, to allow the coating to affix to one or more of internal surfaces of vessel. In embodiments, material is a film applied to one or more of interior surfaces 115, 113, and 112 of each of top wall 110, bottom wall 109 and side walls 112. A film may be applied to one or more of internal surfaces of vessel by any method known in the art, including applying a film to one or more of internal surfaces prior to assembling vessel. In embodiments, material is integral with one or more of the top wall 110, bottom wall 109 and side walls 112. For example, material may be extruded to form one or more of top wall 110, bottom wall 109 and side walls 112.

Figure 4B:
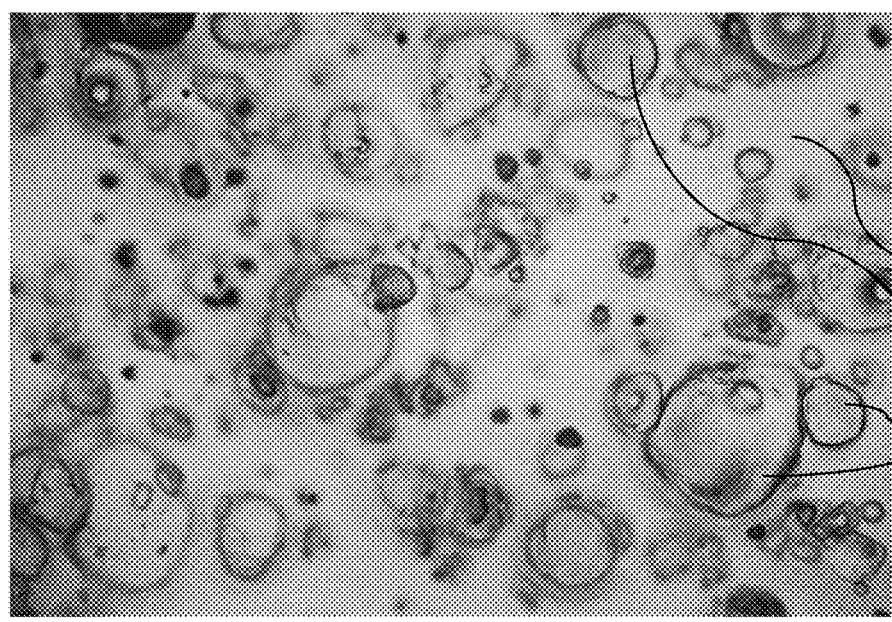

FIGS. 4a and 4b are images of embodiments of cell culture media extending materials 151, in the absence (FIG. 4a) and in the presence (FIG. 4b) of cell culture media. Shown in FIG. 4a is a photograph of an embodiment of the cell culture extending material, a poly(ethylene-co-vinyl acetate) "EVA" material (40% vinyl acetate) with 20% glucose, solvent cast onto a surface. In dry conditions, glucose crystals 300 are visible under a tight layer of polymer 301. As shown in FIG. 4a, glucose crystals are sequestered in the polymer. In embodiments, the polymer, together with its trapped or sequestered nutrients (in the case of FIGS. 4a and 4b, glucose) are cell culture extending materials 151. After incubating the material in aqueous dPBS solution, which is osmotically similar to media, for 96 hours, the material has changed, as shown in FIG. 4b. Without being limited by theory, it is hypothesized that glucose, trapped in the polymer, has absorbed water, creating pressurized pockets 315 in the polymer 301 leading to pumping of the nutrients out of the polymer, into the surrounding solution. This can be described as an osmotic pump, where the nutrients are driven out of the polymer pocket into the media by the concentration gradient between the pocket and the media.

In embodiments of the present invention, a multi-layer flask is provided. An embodiment of the multi-layer flask 100 of the present invention is illustrated in the partial cut-away perspective view shown in FIG. 5. The multi-layer flask 100 has an outer vessel body 101 defined by a top wall 110, a bottom tray (not shown), sidewalls 112, and end walls 114. Disposed within the flask 100 are individual cell growth chambers 111 as can be seen more clearly in FIG. 6. The individual cell growth chambers 111 are each defined by a bottom surface or bed 113 and a top surface or ceiling 115. The surfaces 113 and 115 are attached to the flask body 101 along sidewalls 112 and end walls 114. In embodiments, at least one bottom surface 113 within each chamber 111 is a gas permeable, liquid impermeable material capable of providing a surface for the growth of cells 117. The gas permeable, liquid impermeable material may provide the surface upon which cells attach, or the bed of the cell growth chamber, or it may be the opposite surface, or the ceiling of the cell growth chamber. The bottom surface 113, or the cell culture surface 113 may be flexible or rigid. Each top surface 115, in embodiments, is a rigid, generally gas impermeable material that will provide support to the cell growth chamber 111 and the multi-layer cell culture vessel. The surfaces of the multi-layer flask may be clear, opaque, colored or colorless. In an embodiment of the present invention, there are tracheal spaces 118 between each cell growth chamber 111. The opposing top surface 115 of the chamber 111 defines an upper wall or ceiling to the cell growth chamber 111 as well as a bottom portion of a tracheal chamber 118. The tracheal chamber 118 is therefore inclusive of a gas permeable, liquid impermeable surface 113 of a first cell growth chamber and an opposing surface 115 of a second growth chamber 111. Supports 119 may also be present to provide structural support to integrally incorporate the surfaces 113 and 115 in forming growth chambers 111 in alternation with tracheal air spaces 118 within the unitary flask 101. Each cell growth chamber 111 therefore alternates with a tracheal chamber 118 in vertical successive orientation.

In an embodiment of the present invention, the individual cell growth chambers 111 permit cellular growth on gas permeable membranes 113 such that multiple cell growth chambers 111 are integral with the body 101 of the multi-layer flask 100 and are capable of being completely filled with nutrient media for the growth of cells. In embodiments, these cell growth chambers are approximately 2 mm in height. The series of tracheal air spaces 118 through the multi-layer flask 100 provide gaseous communication between the cells 117 growing on gas permeable surfaces 113, in media 127 in the individual cell growth chambers 111 inside the multi-layer flask, and the external environment. The tracheal spaces 118 allow oxygenation of media located within cell growth chambers 111 through the gas permeable surfaces 113. Further, the tracheal chambers 118 may take the form of any air gap or space, and do not allow entrance of liquid. As a result, a rigid cell culture multi-layer flask 100 having multiple growth chambers 111, alternating with tracheal spaces 118, is cooperatively constructed to afford the benefit of equivalent gaseous distribution to a large volume of cells 117. In embodiments, the multi-layer flask may have ports 120, which may have plugs or port covers 121. In addition, the multi-layer flask may be of any shape. For example, the multi-layer flask may have corners 107.

FIG. 6 is a cross-section of a cell culture vessel 100, taken at plane B-B shown in FIG. 5, showing embodiments 1-5 of the material on interior surfaces of the multi-layer cell culture vessel embodiment shown in FIG. 5. In cell culture chamber 1 (111), a top wall 110 has an interior surface or ceiling 115, and a layer of cell culture media extending material 151 on a bottom surface or bed 113. In embodiments, the bed 113 is made from liquid impermeable, gas permeable film. A tracheal space 118 is below the bed 113, supported by supports 119. In embodiment (1) of the multi-layer cell culture chamber, the cell culture media extending material is on the bottom surface or bed 113.

In cell culture chamber 2, cell culture media extending material is on the interior surface or ceiling 115 of top wall (which in this second layer of the multi-layer is also the layer which provides supports 119 to support gas permeable, liquid impermeable film and form tracheal space 118). In cell culture chambers 3 and 4, material 151 is on side walls. In cell culture chamber 5, cell culture media extending material is on all interior surfaces of the cell culture chamber 111. Those of ordinary skill will understand that cell culture media extending material may be provided on any surface in a cell culture vessel, in the configurations illustrated in FIGS. 1, 2, 3, 5, 6, 7, 8 or any other configuration.

Figure 7:
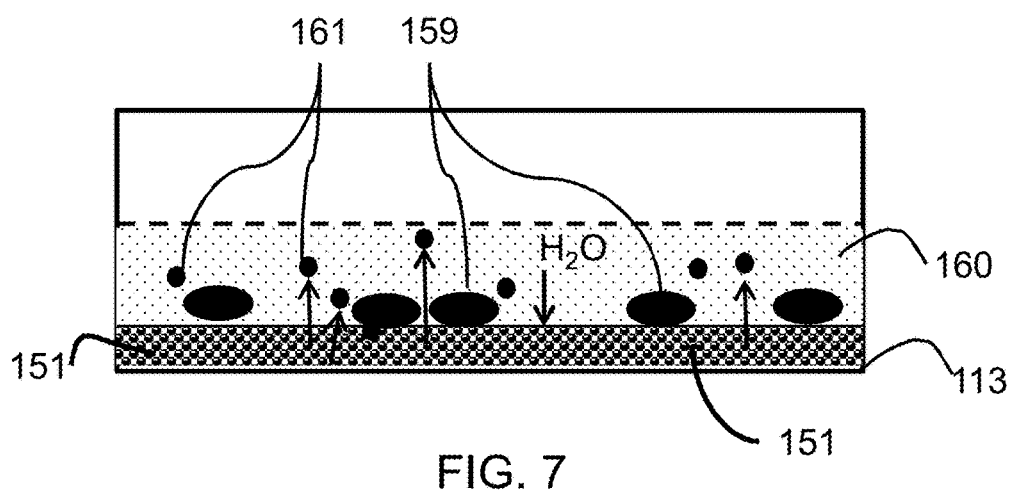
FIG. 7 is an illustration of a method of using the material, in an embodiment.
Figure 8:
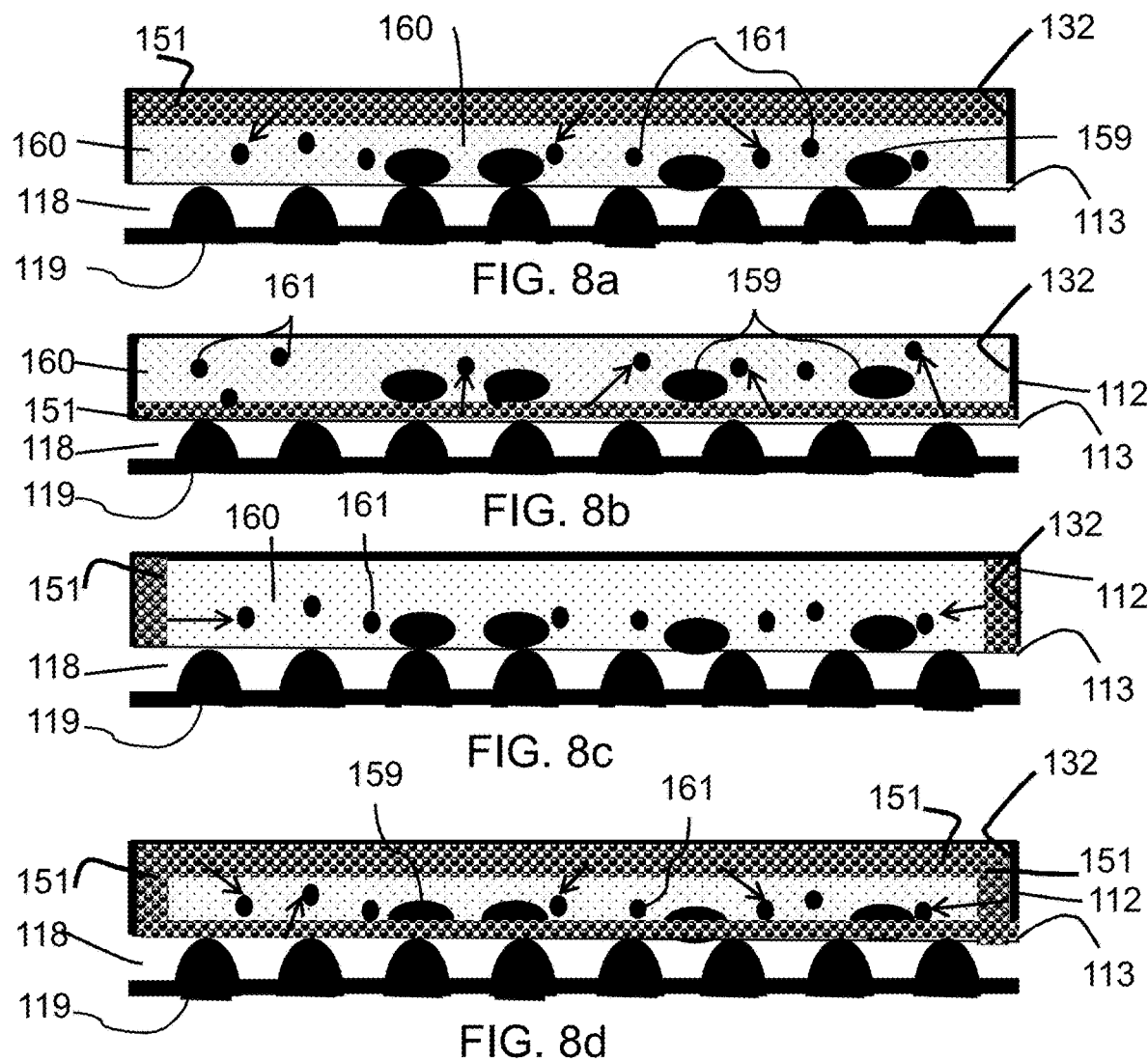
FIGS. 8a-8d are illustrations of embodiments of methods of using four embodiments of the material in a multi-layer flask environment.

FIG. 7 is an illustration of a method of using the material, in a single layer cell culture vessel embodiment. In FIG. 7, cell culture media extending material 151 is on the bottom wall or bed 113 of a cell culture vessel. Cells 159 sit on top of the bed 113, covered with media 160. Nutrients 161 are provided by media, but are also released from cell culture media extending material 151, as shown by arrows in FIG. 7. In addition, water from media 160 enters material 151, as shown by the arrow in FIG. 7. Water may move into the polymer film from the culture media. While not being limited by theories about the mechanism of action of the release of nutrients into media, it may be that water hydrates solid nutrient particles, forming a saturated solution in pockets within the polymer, as shown in FIG. 4b. This solution volume creates pressure within the film which drives the solvated nutrient, which may be, for example, glutamine or glucose, through the polymer and out into the culture media at a steady rate (see FIGS. 14-18). That steady rate maintains a low useful concentration of glutamine to support the cells in culture while keeping ammonium production rates low.

FIGS. 8a-8d are illustrations of embodiments of methods of using four embodiments of the material in a multi-layer flask environment. In FIG. 8a, material 151 is on ceiling 115 of a cell culture chamber in a multi-layer cell culture vessel. Cells 159 sit on top of the bed 113, which may be a liquid impermeable, gas permeable film, covered with media 160. Nutrients 161 are provided by media, but are also released from material 151, as shown by arrows. In addition, water from media 160 enters material 151, (not shown in FIG. 8a, but see FIG. 7, and also FIGS. 4a and 4b). In FIG. 8b, material 151 is on the bottom wall or bed 113 of a cell culture chamber of a multi-layer cell culture vessel. Cells 159 sit on top of the bed 113, covered with media 160. Nutrients 161 are provided by media, but are also released from material 151, as shown by arrows. In FIG. 8c, material 151 is on the interior surfaces 132 of side walls 112 of a cell culture chamber of a multi-layer cell culture vessel. Cells 159 sit on top of the bed 113, covered with media 160. Nutrients 161 are provided by media, but are also released from material 151, as shown by arrows. In FIG. 8d, material 151 is on all of the interior surfaces of a cell culture chamber of a multi-layer cell culture vessel. Cells 159 sit on top of the material 151, on bed 113, covered with media 160. Nutrients 161 are provided by media, but are also released from material 151, as shown by arrows.

In some cell culture vessels, media is provided to the cell culture chamber in a way that provides a layer of air inside the vessel. In this way, oxygen levels are maintained at a health level as oxygen diffuses into the media at the media-air interface. In multi-layer cell culture devices, such as those shown in FIGS. 5 and 6, media fully fills the cell culture chambers. In these embodiments, oxygen is provided to cells in culture by diffusion across a gas permeable liquid impermeable membrane which forms the bed of the cell culture chamber 113. The bed 113 has contact with media on the cell culture chamber side and with air on the tracheal space 118 side of the membrane.

In embodiments, material 151 is provided on the ceiling surface 115 of the cell culture chambers in multi-layer cell culture vessels. In this way, oxygen can diffuse into the cell culture chamber through the gas permeable liquid impermeable membrane of the bed 113 of the cell culture chamber and nutrients can pass into the media via material 151 present on the ceiling of the cell culture chamber.

Examples of cell culture materials for nutrient release include polymers containing sequestered nutrient particles. Suitable polymer material allows water to slowly permeate the polymer material, releasing nutrient particles captured in the polymer matrix. The water is then able to begin dissolving the nutrient particles, freeing the nutrient to be released through the polymer and out of the media. This release of nutrient from the polymer material can act as in response to an osmotic pump, allowing for steady release of glutamine over days.

Polymers useful for the current invention need to be able to contain nutrients. This can be done by mixing the nutrient with polymer materials prior to forming the polymer material into a surface in contact with cell culture media. Nutrients may be in crystal form, and can be captured by or bound in a polymer layer, as shown in FIGS. 4a and 4b. Or, this can be done by providing a layer of polymer between a layer of nutrient and the cell culture media, allowing the nutrients to be released through the polymer layer over time. Or, the nutrients can be trapped between layers of polymer. Nutrients that are trapped beneath a layer of polymer or trapped between layers of polymer are also "sequestered". And, the polymer must be able to release the nutrient at a controlled rate. That is, if the polymer is too porous, nutrients will be released too quickly, on the order of hours. To extend the life of cell culture, nutrients need to be released over a period of days or even weeks. If the polymer is impermeable to water, no nutrients will be released for the benefit of the cell culture. In embodiments, the polymer has characteristics that allow for the release of nutrients at an appropriate rate. One way to describe this characteristic is in the polymer's hygroscopic characteristics. Hygroscopic polymers have an ability to attract and hold water molecules (adsorb water molecules) from the surrounding environment. Examples of hygroscopic polymers include poly(ethylene-co-vinyl acetate), poly(ethyl cellulose), PDMS, poly(ether/amide) copolymers such as PEBAX 2533, and others. Hygroscopic polymers can be distinguished from hydrogels. Hydrogel is defined as "a polymeric material that exhibits the ability to swell and retain a significant fraction of water within its structure, but will not dissolve in water (http://www.sciencedirect.com/science/article/pii/S2090123213000969). A hydrogel is defined by IUPAC as "a gel in which the swelling agent is water" (Notes: 1. The network component of a hydrogel is usually a polymer network. 2. A hydrogel in which the network component is a colloidal network may be referred to as an aquagel.) In general, hydrogels swell in water, and, in water, contain a high percentage of water. For purposes of this disclosure, a hydrogel is a polymer material that swells to more than 50% water by weight in an aqueous environment. In embodiments, the hygroscopic material disclosed herein are polymers that swell to less than 50% water by weight in an aqueous environment. The water-absorbing characteristics and water-releasing characteristics of the polymer determine the rate at which the polymer is able to release nutrients, dissolved in water, over time. Nutrients diffuse out of or through the polymer material.

In embodiments the media extending materials are coatings or films, applied to a cell culture surface, which are capable of releasing cell culture nutrients over time. In embodiments the media extending materials disclosed herein are polymers which swell to less than 50% water by weight in an aqueous environment, which are mixed with nutrients, or have captured or sequestered nutrients, or contain nutrients. In embodiments, nutrients are captured in or sequestered in polymer in crystalline or solid form.

In additional embodiments, the disclosure provides methods of culturing cells in the presence of a cell culture surface having media extending materials where the nutrients, captured in a polymer matrix, dissolve in the presence of aqueous media, and are slowly released into the media. When the nutrients dissolve in an aqueous environment, an osmotic pump may be created in pockets in the polymer matrix, allowing nutrients to flow from the more concentrated environment of the polymer pocket, into the media. This sequestration of nutrients in the polymer matrix allows for the slow introduction of nutrients into media without requiring media changes. This sequestration also allows cells to be cultured, in static culture or in dynamic culture conditions, in the presence of lower concentrations of nutrients which, in higher concentrations, may be toxic to cells, directly or indirectly.

The rate of diffusion of nutrients out of the polymer over time is also affected by the thickness of the film or layers of film, the nature of the nutrients, the diffusion gradient between the polymer and the media, temperature, and other factors.

These polymer/nutrient materials can be made in any form including cast, extruded, molded, or provided as coatings and thin films to provide high surface area for exchange. Also, once films are extruded or made, films can be molded, over-molded, insert-molded or otherwise applied to a surface exposed to cell culture. The material itself can be molded or over-molded to form a surface exposed to cell culture. The material can form at least a part of a surface of a cell culture compartment. The material can form part of a surface that is also the surface upon which cells attach and grow ("cell culture surfaces"), or they may form part of surfaces that are not cell culture surfaces. Or, the material can form at least a part of a microcarrier or other surface used to culture cells.

In embodiments, the material is extruded to form a cell culture vessel. In additional embodiments, the material is formed as a coating on a surface of a cell culture vessel. In additional embodiments, the coating may be a film. The coating may be cast on a surface of a cell culture vessel, or the coating may be formed as a film that is later applied as a film to a cell culture surface. Films can be molded, over-molded, insert-molded or otherwise applied to a surface exposed to cell culture. The formed film may be cast, extruded, or molded, or formed by any other method known in the art. Solvent casting can be used to generate films and coatings.

In additional embodiments, the material is applied in more than one layer to a cell culture surface. For example, a material containing a nutrient can be applied to a surface to form a first layer, and then a second material, which does not contain a nutrient, can be applied on top of the first layer to form a second layer. The application of a second layer which does not contain a nutrient can be applied to slow the release of one or more nutrients from the first layer, as that nutrient has to move out of the first layer, and also through the second layer, before becoming accessible to media (see, for example, Film 19 in Table 1 below).

EXAMPLES

The following examples illustrate the preparation of exemplary materials for enhancing long term cell culture conditions.

Example 1: Formulation of Materials: Film 13 was cast from a 10% solution of poly(ethylene-co-vinyl acetate) (40% VA) in methylene chloride was blended with 20% glucose powder (milled sample) by polymer weight and 20% glutamine by polymer weight. This solution was knifed onto 0.010" thick polystyrene film to a 0.010" thickness which dried to approximately 0.002" thickness. This resulting film was then coated with a 10% solution of the same polymer (EVA) without nutrients added. The final film thickness was 0.013" including the 0.010" polystyrene base film. Film 15 was made the same way but with 20% glucose and 30% glutamine. For layer 4 of film 19, the "overcoat", polymer was dissolved in solvent without the nutrient to form an overcoat. Film 19 was made with an additional basal layer. The first base layer had 40% glucose in EVA followed by another layer with 30% glucose, followed by a layer with 20% glucose and 25% glutamine, followed by the overcoat of EVA without nutrients.

TABLE 1

| Film | Polymer | Glucose | L-glutamine |
|---|---|---|---|
| Film 13 | 10% solution of poly(ethylene-co-vinyl acetate) (40% VA) in methylene chloride | 20% | 20% |
| Film 15 | 10% solution of poly(ethylene-co-vinyl acetate) (40% VA) in methylene chloride | 20% | 30% |
| Film 19 multi-layer material | 10% solution of poly(ethylene-co-vinyl acetate) (40% VA) in methylene chloride | Layer 1: 40% glucose in EVA Layer 2: 30% glucose in EVA Layer 3: 20% glucose and 25% glutamine in EVA Layer 4: (overcoat) EVA without glucose or glutamine | 25% in layer 3 |

Example 2— Formation of Material films: The films profiled in FIGS. 12-18 (discussed below) were solvent cast onto cell culture surfaces. Solvent casting is a process of dissolving a polymer in a suitable solvent. In this example, a suitable solvent is a solvent which dissolves the polymer but not the nutrient. Then the polymer solution is knifed onto a film and allowed to dry. This produces a composite film material having a polymer containing a nutrient. Solid (undissolved) nutrients were present in the film in clumps. That is, because the nutrients were not dissolved in the cast material, they were unevenly distributed throughout the composite polymer material (see FIGS. 4a and 4b). Solvent casting can be used to generate films and coatings. Thermal processing may also be used to provide films of material 151. These films could be inserted into a mold and over-molded with a first polymer layer of the film facing the mold cavity so as to create a weld when the mold is filled with a polymer compatible with the first polymer layer. The osmotic pump side of the film would then be facing the cell culture chamber. The film could also be welded in a secondary operation.

Figure 9:
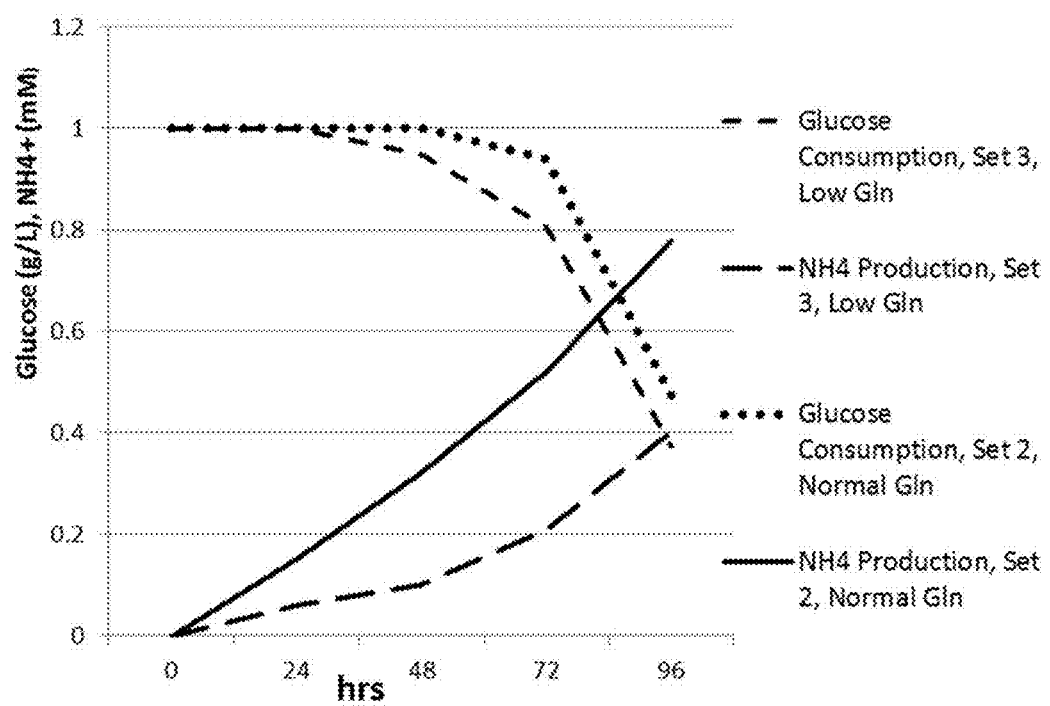
FIG. 9 is a graph showing glucose consumption vs. ammonium production in the presence of traditional media having a 4 mM L-glutamine concentration (and a 1 g/L glucose concentration) compared to experimental low glutamine media conditions having a 0.5 mM L-glutamine concentration (and a 1 g/L glucose concentration).

FIG. 9 is a graph showing glucose consumption vs. ammonium production in the presence of traditional media having a 4 mM L-glutamine concentration (and a 1 g/L glucose concentration) compared to experimental low glutamine media conditions having a 0.5 mM L-glutamine concentration (and a 1 g/L glucose concentration). FIG. 9 illustrates that in low glutamine media conditions, ammonium production is reduced over the 96 hours of culture shown in the graph of FIG. 9. FIG. 9 illustrates that at the end of a 96 hour culture, ammonium production in normal glutamine conditions is approximately twice that measured from cultures in low glutamine conditions. In addition, glucose concentrations fell off faster in low glutamine concentration conditions. Increasing levels of ammonia ($NH_4$) are correlated with decreasingly healthy cell culture conditions. FIG. 9 illustrates that, in the presence of low glutamine, cell culture conditions remain healthier longer. Glucose concentrations fell off faster in the presence of low glutamine concentrations because cell populations increased compared to the normal glutamine conditions (see FIG. 10). Stated another way, cell populations grew up faster under low glutamine conditions than under normal glutamine conditions. This may be due to reduced ammonium build-up (as shown in FIG. 11).

Figure 10:
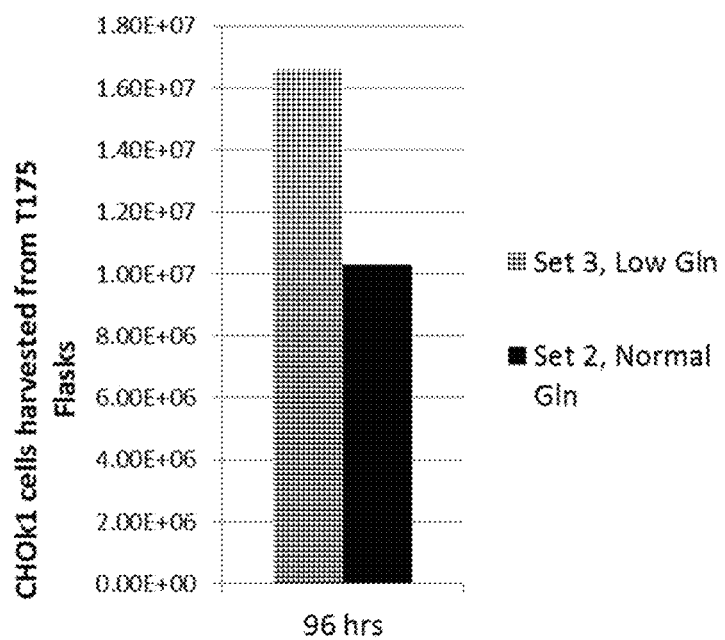
FIG. 10 is a graph illustrating CHOk1 cells harvested after 96 hours growing in traditional media having a 4 mM L-glutamine concentration (and a 1 g/L glucose concentration) compared to experimental low glutamine media conditions having a 0.5 mM L-glutamine concentration (and a 1 g/L glucose concentration).

FIG. 10 is a graph illustrating CHOk1 cells harvested after 96 hours growing in traditional media having a 4 mM L-glutamine concentration (and a 1 g/L glucose concentration) compared to experimental low glutamine media conditions having a 0.5 mM L-glutamine concentration (and a 1 g/L glucose concentration). As shown in FIG. 10, the flasks formulated with low glutamine had an increased yield of cells compared to cells in the presence of normal glutamine conditions. This data, in combination with the graphs shown in FIG. 9 indicate that cells grow faster in low glutamine conditions. This matches reports of batch culture conditions that found cells grew faster in low glutamine/low ammonia culture conditions (*Low-Glutamine Fed-Batch Cultures of 293-HEK Serum-Free Suspension Cells for Adenovirus Production* Lee, Y. Y. et al., Biotechnol. Prog. 2003, 19, 501-509). This group also measured higher viral titer in cells grown in low glutamine/low ammonia conditions. This disclosure shows that in fed-batch cell culture conditions, providing glutamine in batches in low concentrations is favorable.

For the purposes of this disclosure "low glutamine concentration" means a concentration below 2 mM L-glutamine, below 1.5 mM L-glutamine or below 1.0 L-glutamine. Cells need some glutamine in culture, but not very much. That is, L-glutamine concentrations of below 2 mM L-glutamine, below 1.5 mM L-glutamine or below 1.0 L-glutamine are sufficient for supporting cell culture. However, because glutamine breaks down in culture, the levels of glutamine provided in media used for static culture is usually above 2 mM.

Figure 11:
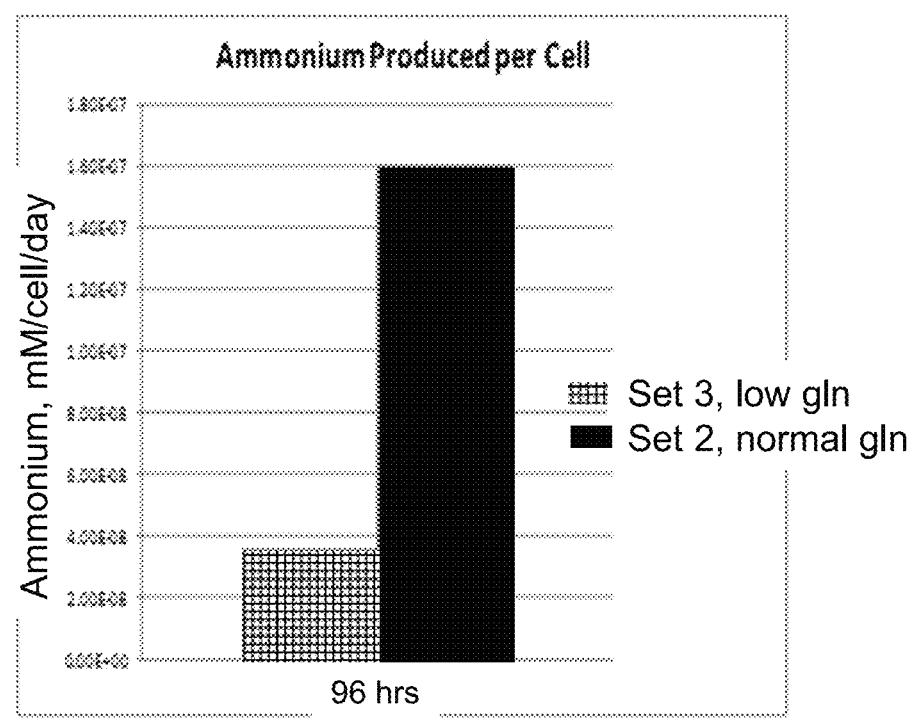
FIG. 11 is a graph illustrating ammonium production per cell per day after 96 hours growing in traditional media having a 4 mM L-glutamine concentration (and a 1 g/L glucose concentration) compared to experimental low glutamine media conditions having a 0.5 mM L-glutamine concentration (and a 1 g/L glucose concentration).

FIG. 11 is a graph illustrating ammonium production per cell per day after 96 hours growing in traditional media having a 4 mM L-glutamine concentration (and a 1 g/L glucose concentration) compared to experimental low glutamine media conditions having a 0.5 mM L-glutamine concentration (and a 1 g/L glucose concentration). Ammonia produced per cell per day (cumulative ammonium produced divided by IVCD, integrated viable cell density) demonstrated an 80% reduction as compared to the standard concentration L-glutamine control (set 2).

Figure 12:
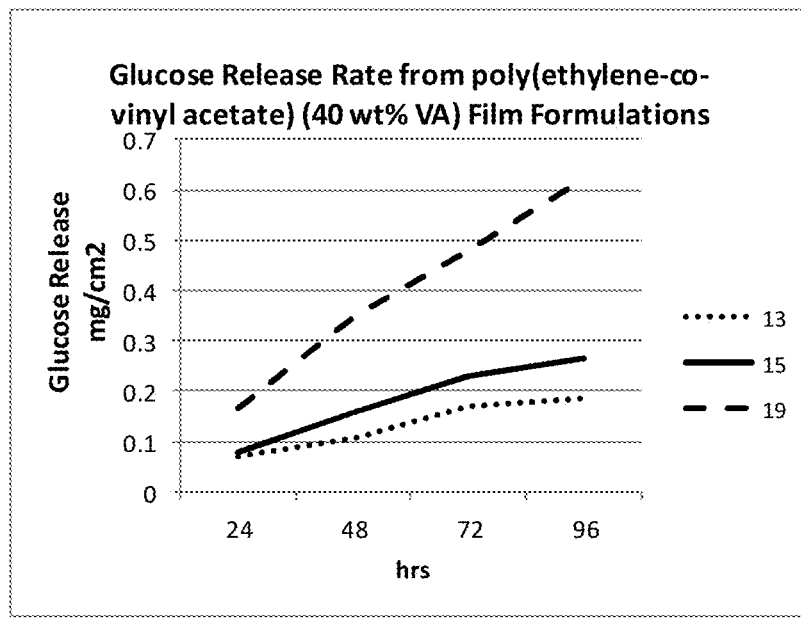
FIG. 12 is a graph illustrating glucose release in mg/cm$^2$ from glucose and glutamine-containing embodiments of the material over time.

FIG. 12 is a graph illustrating glucose release in mg/cm$^2$ from glucose and glutamine-containing embodiments of the material over time. Example of 3 polymer/nutrient film formulations that contains both glucose and glutamine were tested for glucose release. Examples 13, 15 and 19 are defined in Table 1. FIG. 12 plots the release rate of glucose to support cell macro-nutrient requirements and demonstrates that relative changes in the film formulation can result in a wide range of nutrient release rates.

Figure 13:
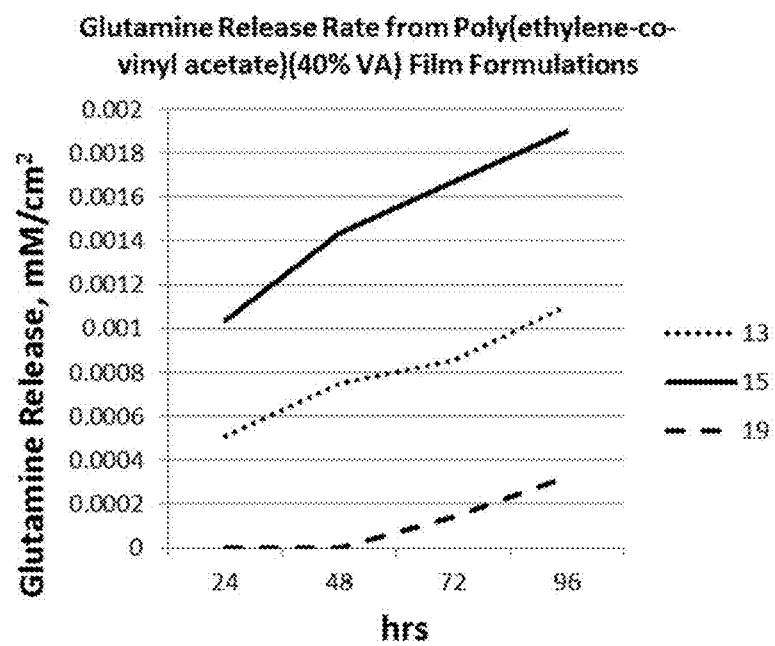
FIG. 13 is a graph illustrating glutamine release in mg/cm$^2$ from glucose and glutamine-containing embodiments of the material over time.

FIG. 13 is a graph illustrating glutamine release in mg/cm$^2$ from glucose and glutamine-containing embodiments of the material over time. Example of 3 polymer/nutrient film formulations that contains both glucose and glutamine (See Table 1 for material compositions). FIG. 13 plots the release rate of L-glutamine to support cell macro-nutrient requirements and demonstrates that relative changes in the film formulation can result in a wide range of nutrient release rates. Depending on the system requirements the formulation can be adjusted to match demand.

Figure 14:
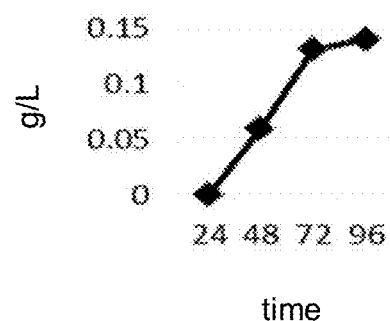
FIG. 14 is a graph illustrating glucose release in g/L from glucose-containing embodiments of the material over time.

FIG. 14 is a graph illustrating glucose release in g/L from glucose-containing embodiments of a material over time in hours. FIG. 14 illustrates glucose release from a PEBAX™ 2533 material containing 10% glucose, and having an additional top coating layer of PEBAX™ without glucose of about 0.001" in thickness. PEBAX™ is a polyamide/polyether block copolymer available from Arkema, King of Prussia, Pa. Material was solvent cast onto cell culture surfaces and incubated in aqueous dPBS solution, which is osmotically similar to media. The concentration of glucose in g/L was measured at time increments. The measured concentration of glucose was multiplied by 3.5 to give equivalent concentration of the released glucose when it enters a 2 mm media head height, resulting in a measurement of average glucose release over time of 0.5 g/L for a 2 mm media height. This media head height is the media space in a multi-layer cell culture flask, the HYPERStack®, available from Corning Incorporated, Corning, N.Y., illustrated in FIG. 5. The PEBAX™ material released glucose at a steady rate of over a 72 hour period of 0.5 g/L.

Figure 15:
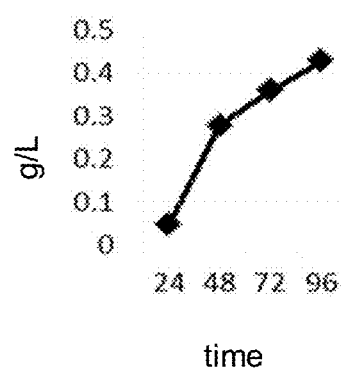
FIG. 15 is a graph illustrating glucose release in g/L from a glucose-containing embodiment of the material over time.

FIG. 15 is a graph illustrating glucose release in g/L from another glucose-containing embodiment of the material over time. FIG. 15 illustrates glucose release from EVA (ethyl vinyl acetate, 40% weight % VA) containing 10% glucose, and having an additional top coating layer of EVA without glucose of about 0.001" in thickness. EVA material was solvent cast onto cell culture surfaces and incubated in aqueous dPBS solution, which is osmotically similar to media. The concentration of glucose in g/L was measured at time increments. The measured concentration of glucose was multiplied by 3.5 to give equivalent concentration of the released glucose when it enters a 2 mm media head height. EVA materials containing glucose released glucose at a steady rate over a 96 hour period 1.5 g/L.

Figure 16:
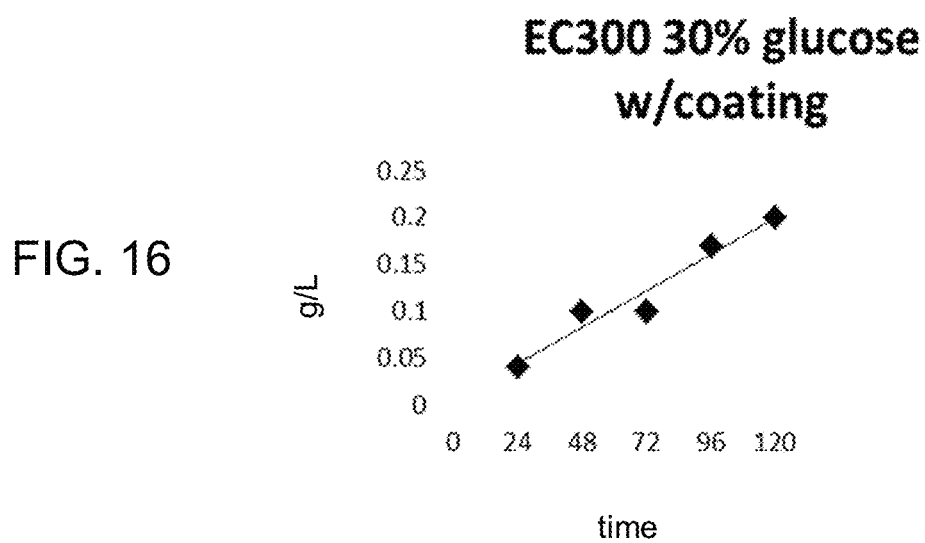
FIG. 16 is a graph illustrating glucose release in g/L from another glucose-containing embodiment of the material over time.
Figure 17:
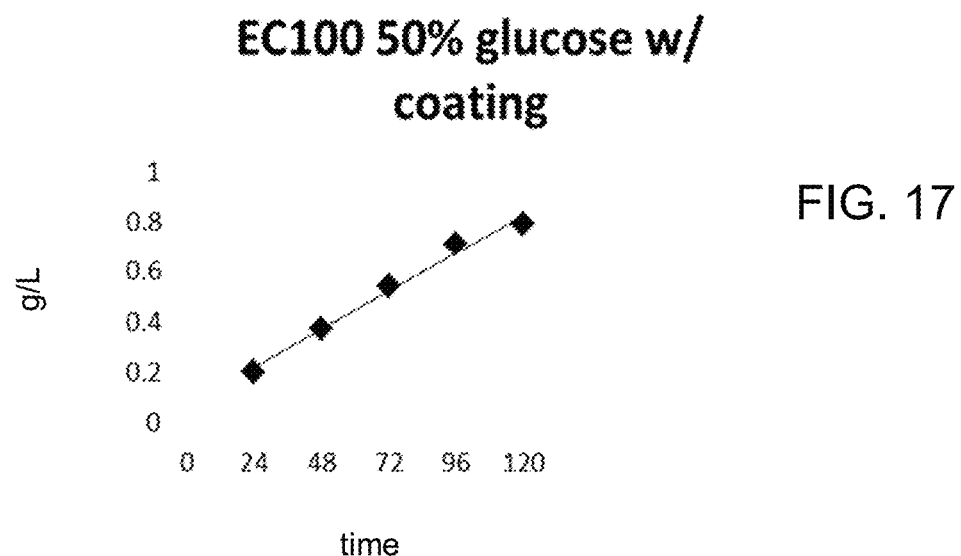
FIG. 17 is a graph illustrating glucose release in g/L from another glucose-containing embodiment of the material over time.

FIG. 16 and FIG. 17 are graphs illustrating glucose release in g/L from a glucose-containing ethyl cellulose embodiment of the material over time. FIG. 15 illustrates glucose release from EC300 grade ethyl cellulose (available from Sigma, Dorset, UK, cat #247499) material containing 30% glucose, and FIG. 16 illustrates glucose release from EC100 grade ethyl cellulose (available from Sigma, Dorset, UK, cat #200654) material containing 50% glucose, each having an additional top coating of polymer without glucose of about 0.001" in thickness. In both cases, material was solvent cast onto cell culture surfaces and incubated in aqueous dPBS solution, which is osmotically similar to media. The concentration of glucose in g/L was measured at time increments. The measured concentration of glucose was multiplied by 3.5 to give equivalent concentration of the released glucose when it enters a 2 mm media head height. Both ethyl cellulose materials containing glucose released glucose at a steady rate over a 120 hour period. The calculated glucose release from the EC300 material having 30% glucose was 0.7 g/L and the calculated glucose release from the EC100 material having 50% glucose was 2.8 g/L.

Figure 18:
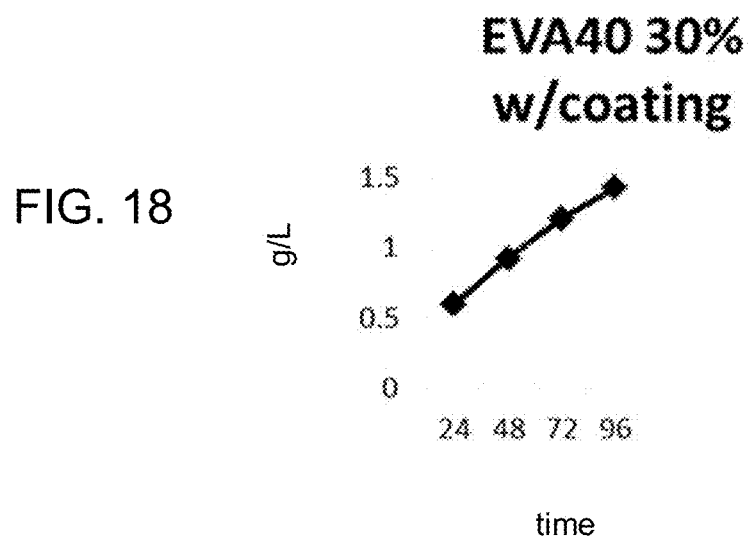
FIG. 18 is a graph illustrating glucose release in g/L from another glucose-containing embodiment of the material over time.

FIG. 18 is an additional graph illustrating glucose release in g/L from another glucose-containing embodiment of the material over time. FIG. 18 illustrates glucose release from EVA (ethyl vinyl acetate, 40% weight % VA) containing 30% glucose and having an additional top coating layer of EVA without glucose of about 0.001" in thickness. EVA material was solvent cast onto cell culture surfaces and incubated in aqueous dPBS solution, which is osmotically similar to media. The concentration of glucose in g/L was measured at time increments. The measured concentration of glucose was multiplied by 3.5 to give equivalent concentration of the released glucose when it enters a 2 mm media head height. EVA materials containing glucose released glucose at a steady rate over a 96 hour period of 4.9 g/L.

The disclosure has been described with reference to various specific embodiments and techniques. However, it should be understood that many variations and modifications are possible while remaining within the scope of the disclosure.

The invention claimed is:

1. A cell culture vessel comprising:
   a surface; and
   a cell culture media extending material disposed on the surface, wherein the cell culture media extending material comprises:
      a first layer disposed between the surface and a second layer, the first layer comprising a hygroscopic polymer and at least one sequestered nutrient;
      the second layer comprising the hygroscopic polymer without the at least one sequestered nutrient, and wherein the hygroscopic polymer comprises poly(ethylene-co-vinyl acetate) (EVA);
      wherein the EVA has an ability to attract and hold water molecules from the surrounding environment;
      wherein the hygroscopic polymers swell to less than 50% water by weight in an aqueous environment; and
      wherein the first and second layers each have a dried thickness of approximately 0.001 inches to approximately 0.002 inches.

2. The cell culture vessel of claim 1, wherein the cell culture media extending material comprises at least one coating.

3. The cell culture vessel of claim 1, wherein the cell culture media extending material comprises a film.

4. The cell culture vessel of claim 1, wherein the vessel comprises at least one cell culture compartment, each cell culture compartment comprising a bed, a ceiling and at least one wall.

5. The cell culture vessel of claim 4, wherein at least two of the bed, the ceiling and the at least one wall comprise the cell culture media extending material.

6. The cell culture vessel of claim 1. wherein the hygroscopic polymer comprises ethyl cellulose materials, poly(ethyl cellulose), PDMS, or poly(ether/amide) copolymers.

7. A cell culture media extending material comprising:
   a first layer comprising a hygroscopic polymer and at least one nutrient; and
   a second layer comprising the hygroscopic polymer without the at least one sequestered nutrient;
   wherein the hygroscopic polymer comprises EVA having an ability to attract and hold water molecules from the surrounding environment;
   wherein the hygroscopic polymers swell to less than 50% water by weight in an aqueous environment; and
   wherein the first and second layers each have a dried thickness of approximately 0.001 inches to approximately 0.002 inches.

8. The cell culture media extending material of claim 7, wherein the material forms part of a cell culture vessel.

9. The cell culture media extending material of claim 7, wherein the material forms at least a part of a microcarrier.

10. The cell culture media extending material of claim 7 wherein the at least one nutrient comprises glucose.

11. The cell culture media extending material of claim 7, wherein the at least one nutrient comprises glutamine.

12. The cell culture media extending material of claim 7, wherein the material is a film.

13. The cell culture extending material of claim 7, wherein the hygroscopic polymer comprises ethyl cellulose materials, poly(ethyl cellulose), PDMS, or poly(ether/amide) copolymers.

14. The cell culture media extending material of claim 7, wherein the at least one nutrient comprises glucose and glutamine.

15. The cell culture extending material of claim 14, wherein the glucose is present at an amount between 20% and 40% glucose by polymer weight and the glutamine is present at an amount between 20% and 30% glutamine by polymer weight.

* * * * *